(12) United States Patent
Bonner, Jr. et al.

(10) Patent No.: US 7,884,090 B2
(45) Date of Patent: Feb. 8, 2011

(54) COMPOSITIONS AND METHODS FOR THE TREATMENT OF ARTHRITIS

(75) Inventors: Ernest L. Bonner, Jr., 1406 Park St., Suite 400, Alameda, CA (US) 94501; Robert Hines, Fayetteville, NC (US)

(73) Assignee: Ernest L. Bonner, Jr., Hillsborough, CA (US)

(*) Notice: Subject to any disclaimer, the term of this patent is extended or adjusted under 35 U.S.C. 154(b) by 1370 days.

(21) Appl. No.: 11/296,575

(22) Filed: Dec. 7, 2005

(65) Prior Publication Data
US 2006/0172956 A1 Aug. 3, 2006

Related U.S. Application Data

(63) Continuation-in-part of application No. 11/096,260, filed on Mar. 29, 2005, which is a continuation-in-part of application No. 11/054,921, filed on Feb. 9, 2005, which is a continuation-in-part of application No. 10/896,612, filed on Jul. 20, 2004, now Pat. No. 7,053,073, which is a continuation-in-part of application No. 10/271,117, filed on Oct. 15, 2002, now Pat. No. 6,765,000, which is a continuation-in-part of application No. 09/510,704, filed on Feb. 22, 2000, now Pat. No. 6,465,473, which is a continuation-in-part of application No. 09/270,962, filed on Mar. 17, 1999, now Pat. No. 6,087,382.

(51) Int. Cl.
*A61K 31/65* (2006.01)
*A61K 31/519* (2006.01)
*A61K 31/44* (2006.01)
*A61K 31/42* (2006.01)
*A61K 31/195* (2006.01)

(52) U.S. Cl. .............. 514/152; 514/262.1; 514/356; 514/398; 514/561

(58) Field of Classification Search ............ 514/152, 514/154, 262.1, 356, 398, 561
See application file for complete search history.

(56) References Cited

U.S. PATENT DOCUMENTS

| | | | |
|---|---|---|---|
| 2,946,801 A | 7/1960 | Fields | |
| 3,148,212 A | 9/1964 | Boothe et al. | |
| 3,226,436 A | 12/1965 | Petisi et al. | |
| 4,177,796 A | 12/1979 | Franco-Vila | |
| 4,521,411 A | 6/1985 | Koloff | |
| 5,262,173 A | 11/1993 | Sheth et al. | |
| 5,523,297 A | 6/1996 | Pruzanski et al. | |
| 5,728,680 A | 3/1998 | Morozov et al. | |
| 5,952,367 A | 9/1999 | Pak | |
| 5,972,389 A | 10/1999 | Shell et al. | |
| 6,034,122 A | 3/2000 | Chayen | |
| 6,087,382 A | 7/2000 | Bonner, Jr. et al. | |
| 6,093,414 A | 7/2000 | Capelli | |
| 6,197,776 B1 | 3/2001 | Bonner, Jr. et al. | |
| 6,326,364 B1 | 12/2001 | Lin et al. | |
| 6,416,779 B1 | 7/2002 | D'Augustine et al. | |
| 6,465,473 B1 | 10/2002 | Bonner, Jr. et al. | |
| 6,765,000 B2 | 7/2004 | Bonner, Jr. et al. | |
| 7,053,073 B2 | 5/2006 | Bonner, Jr. et al. | |
| 2002/0031558 A1 | 3/2002 | Yoo | |
| 2002/0151519 A1 | 10/2002 | Shepard | |
| 2003/0055022 A1 | 3/2003 | Bonner, Jr. et al. | |
| 2005/0059640 A1 | 3/2005 | Bonner, Jr. et al. | |
| 2005/0137181 A1 | 6/2005 | Bonner, Jr. et al. | |
| 2005/0176690 A1 | 8/2005 | Bonner, Jr. et al. | |
| 2006/0172956 A1 | 8/2006 | Bonner et al. | |

OTHER PUBLICATIONS

Lichtman et al., "Reactivation of Arthritis Induced by Small Bowel Bacterial Overgrowth in Rats: Role of Cytokines, Bacteria, and Bacterial Polymers", *Infection and Immunity*, 63(6):2295-2301 (1995).
Schirmer et al., "Acyclovir in Acute Oligoarticular Herpetic Arthritis", *Lancet*, 346(8976):712-713 (1995).
Stebbings et al., "Chickenpox Monoarthritis: Demonstration of Varicella-Zoster Virus in Joint Fluid by Polymerase Chain Reaction", *British Journal of Rheumatology*, 37:311-313 (1998).
Toussirot et al., "Do Minocycline and Other Tetracyclines Have a Place in Rheumatology", *Rev. Rheum Engl. Ed.*, 64(7-9):474-480 (1997).
Acyclovir package Insert from South African Electronic Package Inserts, 3 pages; published Oct. 1, 1997.
Arnold et al., "Poststreptococcal reactive arthritis", *Annals of the Rheumatic Diseases*, 48(8):686-688 (1989).
NDA 05-733 for Zithromax Injection, 218 pages (Azithromycin) dated Jan. 30, 1997.
Swanson, J.M. and Chenitz, W.C., "The prevention and management of genital herpes: a community health approach", *Journal of Community Health Nursing*, 6(4):209-221 (1989).
Tuffrey et al., "The effect of a single oral dose of azithromycin on chlamydial infertility and oviduct ultrastructure in mice", *Journal of Antimicrobial Chemotherapy*, 34:989-999 (abstract only) (1994).
Astrauskiene, D., "Efficacy of empirically prescribed amoxicillin and amoxicillin+ clavulanic acid in children's reactive arthritis: a randomized trial," Clin Exp Rheumatol. Jul.-Aug. 2003;21(4):515-21.
Ayoub et al., "Poststreptococcal Reactive Arthritis," Curr Opin Rheumatol. Jul. 2000;12(4):306-10.
Bardin, T., "Antimicrobial Therapy in Inflammatory Joint Disease," Rev Rhum Engl Ed. Nov. 1998;65(11):625-9.
Bardin et al., "Antibiotic Trials in Reactive Arthritis," Rev Rhum Engl Ed. Jan. 30, 1999;66(1 Suppl):63S-66S.
Bell et al., "Management of sexually acquired reactive arthritis in 19 North Thames GUM clinics," Int J STD AIDS, Mar. 2004;15(3):195-8.

(Continued)

*Primary Examiner*—Raymond J Henley, III
(74) *Attorney, Agent, or Firm*—Brian Beverly; Beeson Skinner Beverly, LLP

(57) ABSTRACT

The present invention provides compositions, combination of medicaments, and methods for the treatment of certain conditions such as arthritis, and in particular, reactive arthritis, osteoarthritis, and bursitis, among others.

42 Claims, No Drawings

OTHER PUBLICATIONS

Birdi et al., "Acute rheumatic feaver and poststreptococcal reactive arthritis: diagnostic and treatment practices of pediatric subspecialists in Canada,": J Rheumatol. Jul. 2001;28(7):1681-8.

Brandt et al., "Effects of doxycycline on progression of osteoarthritis: results of a randomized, placebo-controlled, double-blind trial," Arthritis Rheum. Jul. 2005;52(7):2015-25.

Burnette et al., "Purification and Characterization of a Rat Liver Enzyme that Hydrolyzes Valaciclovir, the $_L$-Valyl Ester Prodrug of Acyclovir," Chem. Abs. AN#1995;673023, J. Biol. Chem., 270(26), 15827-31.

Ceroni et al., "Risks and complications of prolonged parenteral antibiotic treatment in children with acute osteoarticular infections," Acta Orthop Belg. Oct. 2003;69(5):400-4.

Fryden et al., "Early antibiotic treatment of reactive arthritis associated with enteric infections: clinical and serological study," BMJ, Dec. 8, 1990;301(6764):1299-302.

Hopkinson, N., "Sexually-acquired reactive arthritis," Hosp Med. Feb. 2001;62(2):83-5.

Kamphuisen et al., "Two years of penicillin prophylaxis is sufficient to prevent clinically evident carditis in poststococcal reactive arthritis," J Intern Med. Nov. 2001;250(5):449-52.

Kloppenburg et al., "Antimicrobial therapy for rheumatoid arthritis," Baillieres Clin Rheumatol. Nov. 1995;9(4):759-69.

Kocak et al., "Poststretptococcal Reactive Arthritis: Clinical Course and Outcome in 15 Patients," Turk J Pediatri. Apr.-Jun. 2000;42(2):101-4.

Kvien et al., "Three month treatment of reactive arthritis with azithromycin: a EULAR double blind, placebo controlled study," Ann Rheum Dis. Sep. 2005;63(9):1113-9.

Laasila et al., "Antibiotic treatment and long term prognosis of reactive arthritis," Ann Rheum Dis. Jul. 2003;62(7):655-8.

Lehman et al., "Clinical trials for post-streptococcal reactive arthritis," Curr Rheumamtol Rep. Oct. 2001;3(5):363-4.

Leirisalo-Repo, M., "Therapeutic aspects of spondyhloarthropathies—a review," Scand J Rheumatol. 1998;27(5):323-8.

Loffler et al, "*Clostridium difficile*-associated reactive arthritis in two children," Joint Bone Spine. Jan. 2004;71(l):60-2.

Morfin Maciel et al., "Reactive polyarthritis and painful dermatographism caused by *Helicobacter pylori*," Rev Alerg Mex. May-Jun. 2002;49(3):99-102. Article in Spanish; abstract only is provided in English.

Neumayr et al., "Chronic reactive arthritis associated with Calmette-Guerin bacillus," Dtsch Med Wochenschr. Sep. 13, 2002;127(37):1886-8. Article in German; abstract only is provided in English.

Palazzi et al., "Reactive arthritis: advances in diagnosis and treatment," Reumatismo. Apr.-Jun. 2002;54(2):105-12. Article in Italian; abstract only is provided in English.

Palazzi et al., "Management of reactive arthritis,"Expert Opin Pharmacother. Jan. 2004;5(1):61-70.

Pappas et al., "Unusual causes of reactive arthritis: Leptospira and Coxiella bumetii," Clin Rheumatol. Oct. 2003;22(4-5):343-6.

Pott et al. letter, "Long-term antibiotic treatment in reactive arthritis," Lancet. Jan. 30, 1988;1(8579):245-6.

Shulman et al., "Poststreptococcal reactive arthritis," Curr Opin Rheumatol. Sep. 2002;14(5):562-5.

Sieper et al., "Report on the Fourth International Workshop on Reactive Arthritis," Apr. 2000; Arhritis Rheum. 2000, Apr;43(4):720-34.

Sieper, J., "Reactive arthritis: practical procedure in diagnosis and problematic aspects of antibiotic therapy," Z Rheumatol. Apr. 2003;62(2):110-1. Article in German; abstract only is provided in English.

Sieper et al., "No benefit of long-term ciprofloxacin treatment in patients with reactive arthritis and undifferentiated oligoarthritis: a three-month, multicenter, double-blind, randomized, placebo-controlled study," Arthritis Rheum. Jul. 1999;42(7):11386-96.

Sieper et al., "Expert Witness Reports in Rheumatology," British Society for Rheumatology, 1998;37:715-20.

Smieja et al., "Randomised, blinded, placebo controlled trial of doxycycline for chronic seronegative arthritis," Ann Rheum Dis. Dec. 2001; 60(12):1088-94.

Svenungsson, B., "Reactive arthritis," Int J STD AIDS. May-Jun. 1995;6(3):156-60.

Toivanen et al., "Reactive Arthritis," Curr Opin Rheumatol. Jul. 1997;9(4):321-7.

Toivanen et al., "Effect of antimicrobial treatment on chronic reactive arthritis," Clin Exp Rheumatol. May-Jun. 1993;11(3):301-7.

Toivanen et al., "Reactive arthritis," Best Practice & Research Clinical Rheumatology, Oct. 2004;18(5):689-703.

Toivanen, A., "Bacteria-Triggered reactive arthritis: implications for antibacterial treatment," Drugs. 2001;61(3):343-51.

Zhang et al., "Experimental Yersinia-triggered reactive arthritis: effect of a 3-week course of ciprofloxacin," Br J Rheumatol. May 1997;36(5):541-6.

COMPOSITIONS AND METHODS FOR THE TREATMENT OF ARTHRITIS

CROSS REFERENCE TO RELATED APPLICATIONS

This application is a continuation-in-part of U.S. application Ser. No. 11/096,260, filed on Mar. 29, 2005, which is a continuation-in-part of U.S. application Ser. No. 11/054,921, filed on Feb. 9, 2005, which is a continuation-in-part of U.S. application Ser. No. 10/896,612, filed on Jul. 20, 2004, now U.S. Pat. No. 7,053,073, which is a continuation-in-part of U.S. application Ser. No. 10/271,117, filed on Oct. 15, 2002, now U.S. Pat. No. 6,765,000, which is a continuation-in-part of U.S. application Ser. No. 09/510,704, filed on Feb. 22, 2000, now U.S. Pat. No. 6,465,473, which is a continuation-in-part of U.S. application Ser. No. 09/270,962, filed on Mar. 17, 1999, now U.S. Pat. No. 6,087,382, each of which is incorporated herein by reference in its entirety.

FIELD OF THE INVENTION

The present invention relates generally to compositions, combinations of medicaments, and methods for the treatment of certain conditions such as seronegative arthritis, and in particular, reactive arthritis, osteoarthritis, and idiopathic bursitis, among others.

BACKGROUND OF THE INVENTION

Arthritis is a family of diseases resulting in inflammation and pain at body joints and possibly other internal organs. The effects of arthritis can be debilitating to a subject's quality of life; effective treatments for many members of the arthritis-family of diseases are limited and are of varying degrees of effectiveness.

In looking at the spectrum of diseases making up the arthritis family, a small percentage, i.e., approximately 5%, of arthritis patients have rheumatoid arthritis (RA). RA patients often possess certain markers of the disease, i.e., are seropositive for RA factor and exhibit an elevated erythrocyte sedimentation rate and anti-nuclear antibodies. Thus, rheumatoid arthritis is an arthritic condition that can usually be readily diagnosed. Typically, RA patients are treated with non-steroidal anti-inflammatory drugs (NSAIDs), disease-modifying anti-rheumatic drugs (DMARDs), corticosteroids, or newer biologics that block specific hormones involved in the inflammatory process.

Reactive arthritis (ReA), formally considered as yet another type of arthritis, can develop following a microbial infection in an area in the body outside of the affected joint or joints (i.e. a distant infection), such as in the genitourinary or intestinal tract. Known triggering microbes include, e.g., *Chlamydia trachomatis*, *Yersinia enterocolitica*, *Salmonella*, *Shigella*, *Campylobacter*, *Neisseria*, *Ureaplasma urealyticum*, and *Streptococcus pyogenes*, to name a few of the most frequently-associated microbes. Most often, the inflamed joint or joints possess no cultivable microbes. In instances in which the genitourinary tract, eyes, skin or muscles are also affected, ReA may be referred to as Reiter's Syndrome.

Another approximately 3-4% of arthritis patients, including reactive arthritis patients, have syndromes such as ankylosing spondylitis and psoriatic arthritis. Ankylosing spondylitis (AS) is a syndrome that mainly affects the spine but can also affect other joints, tendons and ligaments. AS is a painful, progressive, rheumatic disease. In patients suffering from AS, inflammation occurs at the site where certain ligaments or tendons attach to bone (enthesis). This is followed by some erosion of bone at the site of the attachment (enthesopathy). As the inflammation subsides, a healing process takes place and new bone develops. Movement becomes restricted where bone replaces the elastic tissue of ligaments or tendons. Repetition of this inflammatory process leads to further bone formation and the individual bones that make up the backbone, i.e., the vertebrae, often fuse together.

Psoriatic arthritis is another syndrome-type of arthritis that causes pain and swelling in some joints, and scaly skin patches on some areas of the body. It is related to the skin condition psoriasis; its cause is unknown.

The remainder of arthritis patients suffer from osteoarthritis (OA) and other arthropathies. Approximately 50% of all patients suffering from arthritic disease possess osteoarthritis, a type of arthritis that is associated with a breakdown of cartilage in body joints. This disease causes pain and difficulty in bone movement. Associated pain can also result from involvement of muscles and other tissues, i.e., tendons and ligaments, at diseased joints. Typical therapies for the treatment of OA include the administration of painkillers, NSAIDs and corticosteroids. Although not to be bound or limited by theory, it is the inventors' belief that reactive or enthesopathic arthritis is a precursor to osteoarthritis in a majority of patients diagnosed with osteoarthritis. In such cases, it is believed that following an initial triggering infection, a low level microbial infection persists, but often goes unnoticed or undetected for an extended period of time, often several years, until it has caused enough joint destruction to be classified as osteoarthritis.

The diagnosis of reactive arthritis by clinicians can be extremely difficult, as no overall agreement exists within the medical community on general guidelines setting forth diagnostic criteria for ReA. Further, patients are often unaware of the occurrence of the triggering infection, e.g., in the case of an often-asymptomatic infection such as genital *Chlamydia trachomatis*. Moreover, patients suffering from ReA are seronegative for any blood markers, further complicating its proper diagnosis.

Symptoms associated with ReA may include one or more of the following: joint discomfort, skin and mucous membrane symptoms, gastrointestinal manifestations, and ocular lesions. The most common symptom is joint discomfort, where the most commonly affected joints are those of the lower extremities, such as the knee, ankle, and joints of the foot. Additional symptoms may include fatigue, malaise, fever, weight loss, urethritis and prostatitis in males, and cervicitis or salpingitis in females.

As is evident from the above, reactive arthritis is a serious condition that can be extremely painful. Long term follow-up studies have indicated that 20-70% of patients with ReA later suffer from joint discomfort or other symptoms (Toivanen, A. and Toivanen, P., *Best Practice & Research Clinical Rheumatology*, Vol 18, No. 5, p. 689-703 (2004). Commonly employed treatments for ReA include the administering of NSAIDs, disease-modifying anti-rheumatic drugs, and corticosteroids. The administration of such drugs is typically aimed at managing the pain and inflammation associated with ReA.

Several studies have examined the use of antibiotics in the treatment of reactive arthritis (Sieper, J., Braun, J., *British Journal of Rheumatology* 1998; 37:717-720 and references cited therein). Most of the studies to date have employed the use of a single antibiotic such as tetracycline, lymecycline (Lauhio, A., et al., *Arthritis Rheum* 1001: 34:6-16), or ciprofloxacin (Toivanen A., et al., *Clin Exp Rheumatol* 1993; 11:301-7). However, none of these studies has concluded an advantage or has recommended long-term treatment of ReA with antibiotics. Rather, the majority of studies have found antibiotics to be of limited or of no use in the treatment of ReA. (Sieper, J., Braun, J., ibid).

Yet another painful inflammatory condition is bursitis. Bursitis is inflammation of a bursa—a small, fluid-filled sac lined with synovial tissue. There are over one hundred fifty bursae in the human body. These bursae lubricate and cushion pressure points between the bones and the tendons, and their function is to facilitate movement of tendons and muscles over bony prominences. Bursitis may be caused by excessive frictional forces, trauma, systemic disease such as rheumatoid arthritis or gout, or infection. Many times, its cause is unknown.

Treatment of bursitis generally includes resting and immobilizing the affected area, applying ice to reduce swelling, and taking non-steroidal anti-inflammatory drugs to reduce pain and inflammation. In certain instances, a corticosteroid is administered to relieve inflammation; oftentimes, relief is immediate. In instances in which the bursitis is caused by infection, a single antibiotic may be administered. Unfortunately, with the currently available treatment regimes, recurrent flare-ups are common, and can be extremely frustrating as well as painful. Over a long term, bursitis can result in loss of joint use and chronic pain syndrome. Thus, the long-term adverse effects of bursitis can range from chronic pain to crippling disability.

In sum, currently known therapies for the treatment of diagnosed reactive arthritis, osteoarthritis, and bursitis have been of a limited, if any, well-accepted degree of success. Based upon the on-going research focused on reactive arthritis, it can be seen that there is a need for an effective therapy for the treatment of reactive arthritis and osteoarthritis (herein considered a consequence of reactive arthritis). There also exists a need for an effective therapy for treating other inflammatory conditions such as bursitis. In particular, there is a need for compositions and treatments effective to significantly ameliorate or ideally, eliminate, joint pain, tenderness, stiffness, and fatigue associated with one or more of the above conditions. The present invention meets this need.

SUMMARY OF THE INVENTION

Accordingly, in one aspect, the invention provides a pharmaceutical composition effective in the treatment of conditions such as reactive arthritis, osteoarthritis, or idiopathic bursitis, among others. The composition comprises a combination of at least two of: (i) an antiviral compound, (ii) a broad-spectrum antibiotic, and (iii) an antiprotozoal compound.

In one embodiment, the composition of the invention comprises an antiviral compound and a broad-spectrum antibiotic.

In another embodiment, the composition comprises an antiviral compound and an antiprotozoal compound.

In yet another embodiment, the composition comprises a broad-spectrum antibiotic and an antiprotozoal compound.

In a preferred embodiment, the composition comprises each of (i) an antiviral compound, (ii) a broad-spectrum antibiotic, and (iii) an antiprotozoal compound.

Antiviral compounds for use in the invention include nucleoside analogues, reverse transcriptase inhibitors, protease inhibitors, and entry inhibitors.

In one embodiment, the antiviral compound is a nucleoside analogue such as acyclovir, gancyclovir, pencyclovir, famcyclovir, valacyclovir, valgancyclovir, dideoxyinosine, adefovir dipivoxil, tenovir disoproxil, brivudin, cidofovir, zidovudine, lamivudine, stavudine, zalcitabine, and didanosine.

In a preferred embodiment, the antiviral compound is acyclovir or valacyclovir.

Broad spectrum antibiotic compounds for use in the invention include aminoglycosides, macrolides, ketolides, quinolones, tetracyclines, sulfonamides and beta-lactams.

In a particular embodiment of the invention, the broad spectrum antibiotic is a tetracycline selected from the group consisting of tetracycline, chlortetracycline, doxycycline, meclocycline, minocycline, demeclocycline, methacycline, tigecycline, and oxytetracycline.

In yet a further embodiment, an antiprotozoal compound contained in a composition or combination of the invention is effective against anaerobic bacteria and/or protozoa. Particularly preferred antiprotozoal compounds for use in the invention belong to the nitroimidazole class. Nitroimidazoles for use in the invention include metronidizole, ornidazole, secnidazole, and tinidazole. Additionally, antiprotozoals such as pentamidine may be employed, among others.

In yet another embodiment, a composition or combination of the invention comprises a nucleoside analogue, a tetracycline, and a nitroimidazole.

In a further embodiment, a composition or combination in accordance with the invention comprises a combination of at least two of: (i) an antiviral compound, (ii) a broad-spectrum antibiotic, and (iii) an antiprotozoal compound, where each of the components is either contained in a single composition or dosage form (such as in an admixture), or is present as a discrete or separate entity.

A composition of the invention may optionally include one or more pharmaceutically acceptable excipients.

In yet another embodiment, the composition of the invention is in a form suitable for oral or parenteral administration, e.g., a tablet, capsule, oral suspension, or injectable.

In yet another aspect, the invention encompasses a kit comprising a combination of medicaments for the treatment of reactive arthritis or osteoarthritis, comprising at least two of: (i) an antiviral compound, (ii) a broad-spectrum antibiotic, and (iii) an antiprotozoal compound, for simultaneous, sequential or separate use.

Another aspect of the invention encompasses a method of preparing a combination effective in the treatment of reactive arthritis or osteoarthritis. The method comprises the step of combining a pharmaceutically effective amount of at least two of: (i) an antiviral compound, (ii) a broad-spectrum antibiotic, and (iii) an antiprotozoal compound, to thereby provide an anti-arthritic or anti-osteoarthritic combination, e.g., for treating ReA or OA.

In one embodiment of the above method, the combining step comprises combining each of the compounds into a single administrable formulation, for example, in a form suitable for oral or parenteral administration.

In yet another embodiment, the combining step further comprises the addition of one or more pharmaceutically acceptable excipients.

In an alternative embodiment of the method, the combining step comprises combining each of the compounds into a kit, wherein each of the compounds is for simultaneous, sequential or separate use.

In a further aspect, the invention provides a method for the treatment of reactive or osteoarthritis. The treatment method comprises administering to a mammalian subject suffering from one or more of the following symptoms: stiffness, joint pain, joint tenderness, spine pain, spine tenderness, enthesopathy, and fatigue, a therapeutically effective amount of at least two of: (i) an antiviral compound, (ii) a broad-spectrum antibiotic, and (iii) an antiprotozoal compound, over a duration of time effective to result in a diminution of the one or more symptoms.

In a preferred embodiment of the treatment method, the administering is over a duration of time effective to result in substantial elimination of the one or more symptoms.

In yet another embodiment, the method comprises administering a therapeutically effective amount of each of (i) an antiviral compound, (ii) a broad-spectrum antibiotic, and (iii) an antiprotozoal compound to a mammalian subject.

Each of the herein-described features of the invention is meant to apply equally to each and every embodiment as described herein, unless otherwise indicated.

Additional objects, advantages and novel features of the invention will be set forth in the description that follows, and in part, will become apparent to those skilled in the art upon reading the following, or may be learned by practice of the invention.

DETAILED DESCRIPTION OF THE INVENTION

I. Definitions

Before describing the present invention in detail, it is to be understood that this invention is not limited to particular drugs, combinations of drugs, administration modes, and the like, as such may vary, as will be apparent from the accompanying description.

It must be noted that, as used in this specification and the intended claims, the singular forms "a," "an," and "the" include plural referents unless the context clearly dictates otherwise. Thus, for example, reference to "a drug" includes a single drug as well as two or more of the same or different drugs, reference to "an optional excipient" refers to a single optional excipient as well as two or more of the same or different optional excipients, and the like.

In describing and claiming the present invention, the following terminology will be used in accordance with the definitions described below.

"Pharmaceutically acceptable excipient or carrier" refers to an excipient that may optionally be included in the compositions of the invention and that causes no significant adverse toxicological effects to the patient.

"Pharmacologically effective amount," "physiologically effective amount," and "therapeutically effective amount" are used interchangeably herein to mean the amount of a drug or drug-combination that is needed to provide a desired level of drug in the bloodstream or in the target tissue. The precise amount will depend upon numerous factors, e.g., the particular drug or drugs employed, the components and physical characteristics of the therapeutic composition, intended patient population, individual patient considerations, and the like, and can readily be determined by one skilled in the art, based upon the information provided herein.

"Pharmaceutically acceptable salt" includes, but is not limited to, amino acid salts, salts prepared with inorganic acids, such as chloride, sulfate, phosphate, diphosphate, hydrobromide, hydrochloride, and nitrate salts, or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

"Active molecule" or "active agent" as described herein includes any agent, drug, compound, composition of matter or mixture which provides some pharmacologic, often beneficial, effect that can be demonstrated in-vivo or in vitro. This includes foods, food supplements, microbiologicals, nutrients, nutriceuticals, drugs, vaccines, antibodies, vitamins, and other beneficial agents. As used herein, the terms further include any physiologically or pharmacologically active substance that produces a localized or systemic effect in a patient.

"Substantially" or "essentially" means nearly totally or completely, for instance, 95% or greater of some given quantity. For example, a substantial elimination of one or more symptoms or clinical indicators, e.g., of reactive arthritis or osteoarthritis, means a reduction in severity of 95% or more of a symptom such as stiffness, joint pain, joint tenderness, spine pain, spine tenderness, fatigue, as assessed by any clinically acceptable method, or an improvement of at least 95% of a given clinical indicator.

A "diminution" of one or more symptoms or clinical indicators, e.g., of reactive arthritis or osteoarthritis, or a related inflammatory condition, means a measurable reduction in the severity of such one or more symptoms, as assessed by any clinically acceptable method, or a measurable improvement of a given clinical indicator, as assessed by a skilled clinician.

The term "patient," refers to a living organism suffering from or prone to a condition that can be prevented or treated by administration of a drug or combination of drugs of the invention, and includes both humans and animals.

"Optional" or "optionally" means that the subsequently described circumstance may or may not occur, so that the description includes instances where the circumstance occurs and instances where it does not.

II. Pharmaceutical Compositions

As described previously, the inventors have discovered a unique combination of certain classes of drugs that are remarkably effective in the treatment of certain inflammatory conditions such as reactive arthritis, osteoarthritis, bursitis, and the like. The compositions and combinations of the invention include at least two of, and preferably include each of: (i) an antiviral compound, (ii) a broad-spectrum antibiotic, and (iii) an anti-protozoal compound.

When administered individually, drugs belonging to each of the above classes afford minimal or negligible effect on the manifestations of reactive and osteoarthritis or bursitis. However, in each of the instances in which the applicants have administered a therapeutic drug combination of the invention to a patient suffering from one or more of the following symptoms: stiffness, joint pain, joint tenderness, spine pain, spine tenderness, enthesopathy, and fatigue, following a course of treatment, the patient has reported at least a remarkable and measurable reduction in the severity of each of the symptoms, and in some instances, has described complete alleviation of some if not all of the symptoms. See, for example, Examples 1-13 herein, which demonstrate at least a symptom-modifying response, and most likely a disease-modifying response, to the combination of drugs administered.

Recently, clinicians have become more aware of reactive arthritis and the role of infection in its etiology, and as a result, patients are sometimes administered a short course of an antibiotic. It has been concluded, however, that there is no solid evidence to support such a practice (Toivanen A., Toivanen, P., *Best Practice & Research in Clinical Rheumatology*, Vol. 18, No. 5, 689-703, 2004). In fact, current recommendations indicate antibiotic treatment only in cases where the triggering agent can still be demonstrated. Once reactive arthritis has developed, administration of an antibiotic is thought to be of little or no immediate value (Toivanen, A., Toivanen, P., ibid).

Although antibiotic treatment alone has been found to have no real value in the treatment of reactive arthritis or osteoarthritis, the inventors have discovered a surprising combination of particular drug classes to be extremely effective in ameliorating, and in some cases completely eliminating the symptoms of reactive arthritis and osteoarthritis. Patients are often concerned over the development of a chronic progressive disease, which can often result in depression, loss of mobility and subsequent weight gain, with the associated development of diabetes, heart disorders, and other disease processes. The debilitating effects of reactive arthritis and osteoarthritis and related disease states can obviously adversely affect a patient's quality of life—thus making proper diagnosis and effective treatment essential.

While extremely effective therapies are unknown to date, the inventors have discovered that administration of an antimicrobial combination of an antiviral compound, a broad-spectrum antibiotic, and an antiprotozoal compound, or any two of the foregoing, is surprisingly effective in treating reactive arthritis and osteoarthritis. As can be seen in the supporting examples, patients suffering from multiple joint pain and stiffness, difficulty in walking, standing, running, or bending, joint swelling, sausage-shaped digits, difficulty in grasping, etc., reported significant, if not remarkable, improvements in their symptoms after a course of therapy with one of the herein-described anti-arthritic combinations.

The compositions, combinations, and methods of the invention will now be described in detail in the sections that follow.

II. A. Antiviral Compound

Antiviral compounds for use in the invention include various types of antivirals such as nucleoside analogues (nucleoside analogue reverse transcriptase inhibitors, NRTIs), reverse transcriptase inhibitors (non-nucleoside reverse transcriptase inhibitors, NNRTIs), protease inhibitors (P is), and neuroaminidase inhibitors, among others. As used herein, an antiviral drug is one that is typically used to treat or is effective in the treatment of a viral infection. An antiviral drug for use in the invention may act by any of a number of different mechanisms. For example, the antiviral may act by interfering with a virus's ability to enter a host cell and replicate itself with the host cell's DNA. Alternatively, the antiviral drug may block the virus's attachment or entry into the cell or may inhibit replication or prevent the virus from shedding the protein coat that surrounds the viral DNA.

Antiviral drugs of particular use in the present invention, that is to say, antiviral drugs that are effective in the treatment of reactive arthritis, osteoarthritis, and other inflammatory conditions when administered in combination with one or more other types of drugs as set forth herein, are those that are effective in the treatment of viruses such as HIV, herpes virus, influenza, cytomegalovirus, hepatitis, rhinovirus, and enterovirus.

Nucleoside Analogues. Nucleoside analogues are one preferred chemical type of antiviral for use in the compositions and methods of the present invention. Nucleoside analogues are synthetic molecules that mimic the naturally occurring nucleosides; most typically, this class of antiviral compounds interferes with the activity of viral enzymes, e.g., reverse transcriptase and viral polymerase, and is used in the treatment of viral infections such as HIV, herpes virus, and cytomegalovirus. Nucleoside analogues for use in the invention include compounds such as acyclovir, gancyclovir, pencyclovir, idoxuridine, trifluridine, brivudin, adenosine arabinoside, famcyclovir, valacyclovir, valgancyclovir, dideoxyinosine (ddI), adefovir, adefovir dipivoxil, tenofovir, tenovir disoproxil, cidofovir, zidovudine (AZT), lamivudine, stavudine, and zalcitabine, and prodrugs, pharmaceutically acceptable derivatives, salts, and metabolites of any of the foregoing.

One type of prodrug, an ester prodrug, or even more particularly, an amino acid ester prodrug, is particularly preferred. Ester prodrugs are suitable prodrug forms for drugs which, when in unmodified form, contain either a carboxylic acid functionality or an alcohol moiety suitable for transformation to an ester functionality. In this way, the ester prodrug, subsequent to administration, is typically hydrolyzed in vivo to release the parent drug. Also preferred are phosphate esters. Often, a prodrug form advantageously improves upon one or more properties of the parent drug. Such properties include increased aqueous solubility, ease of formulation, and improved release profile, to name a few. Many nucleoside analogues themselves are prodrugs that enter cells and are anabolized to their active diphosphate and triphosphate derivatives either by the viral thymidine kinase and/or cellular kinases.

In one embodiment of the invention, the antiviral is a purine-based nucleoside analogue such as acyclovir (commercially available under the brand name, Zovirax®), gancyclovir (Cytovene®), pencyclovir (Denavir®), adenosine arabinoside, famcyclovir (Famvir®), valacyclovir (Valtrex®), valgancyclovir (Valcyte®), adefovir, tenofovir, adefovir dipivoxil (Hepsera®), tenofovir disoproxil (Viread®), entecavir, or dideoxyinosine (Videx®). Compounds belonging to this antiviral subclass contain a purine or derivatized purine ring structure, that is to say, a fused pyrimidine-imidazole ring structure. Of the above, the majority of compounds with the exception of adenosine arabinoside and entecavir are acyclic nucleoside analogues, that is to say, possess either a truncated open sugar ring structure or a phosphonate group or derivative in place of the phosphate moiety. Particularly preferred compounds for use in the invention include the nucleoside analogues, acyclovir and valacyclovir, among others. Examples 1, 2, 6, 8, 9, 10, 11, 12, and 13 demonstrate the use of representative antiviral compounds such as acyclovir and valacyclovir, in combination with other drugs such as minocycline and metronidazole, in the treatment of reactive arthritis or osteoarthritis and their associated symptoms.

In yet another embodiment, the antiviral compound is a thymidine-based nucleoside analogue, that is to say, an antiviral compound possessing a thymidine or derivatized thymidine ring structure. These antiviral drugs are typically classified functionally as nucleoside analogue reverse transcriptase inhibitors or NRTIs. Antivirals belonging to both these chemical and functional classes include idoxuridine (Herplex®), trifluridine (Viroptic®), brivudin (Zostex®, Zerpex®), cidofovir (Vistide®), zidovudine (Retrovir®), lamivudine (Epivir®), stavudine (Zerit®), and zalcitabine (Hivid®). Of the antivirals belonging to this class, the only acyclic compound is cidofovir.

In referring to functional rather than chemical class, antivirals for use in the invention include the NRTIs zidovudine, dianosine, zalcitabine, stavudine, lamivudine, abacavir, emtricitabine, and tenofovir (PMPA) disoproxil fumarate. As described previously, these drugs inhibit viral RNA-dependent DNA polymerase and are incorporated into viral DNA.

Also for use in the invention is a nucleoside analogue such as emivirine (also known as MKC-442). Emivirine is a unique nucleoside analogue since its structure is closest to a nucleoside analogue although it is classified functionally as a NNRTI (non-nucleoside reverse transcriptase inhibitor). Another name for emivirine is MKC-442.

NON-NUCLEOSIDE REVERSE TRANSCRIPTASE INHIBITORS. Further antivirals for use in the compositions and methods of the invention include additional antivirals belonging to the NNRTI functional category. NNRTIs are drugs that function by interrupting reverse transcription by binding to the reverse transcriptase enzyme and restricting its activity. Such drugs include tivirapine, nevirapine (Viramune®), a dipyrido-diazepinone; efavirenz (Sustiva®), delavirdine (Rescriptor®), a bis(heteroaryl)piperazine; and capravirine (also known as AG-1549 and S-1153).

PROTEASE INHIBITORS. Antivirals for use in the invention also include protease inhibitors such as the following peptide analogues. Such compounds include saquinavir (Invirase®, Fortovase®), ritonavir (Norvir®), indinavir (Crixivan®), nelfinavir (Viracept®), amprenavir (Agenerase®), lopinavir (Kaletra®), and atazanavir (Reyataz®). A protease inhibitor functions to block the action of protease, an enzyme that cuts HIV protein chains into specific proteins needed to assemble a new copy of the virus.

OTHER ANTIVIRALS. Additional antiviral compounds for use in the invention include drugs effective in the treatment of certain types of influenza such as the tricyclic amines, amantadine (Symmetrel®) and rimantadine (Flumadine®); as well as Neu-5Ac2en (and its C4-substituted derivatives), zanamivir (Relenza®), and oseltamivir (Tamiflu®) in addition to drugs such as methisazone (Marboran®), an antiviral compound effective against pox virus.

ENTRY INHIBITORS. Entry inhibitors such as T-20 (also known as enfuvirtide and Fuzeon®) can also be used in the compositions and methods of the present invention. T-20 functions as an HIV entry inhibitor. Rather than working against HIV post T-cell infection, an entry inhibitor actually prevents HIV from infecting a T-cell in the first place. More specifically, entry inhibitors work by attaching themselves to proteins on the surface of T-cells or proteins on the surface of HIV. In order for HIV to bind to T-cells, the proteins on HIV's outer coat must bind to the proteins on the surface of T-cells. Entry inhibitors prevent the occurrence of such binding. Some entry inhibitors target the gp120 or gp41 proteins on HIV's surface, while other entry inhibitors target the CD4 protein or the CCR5 or CXCR4 receptors on a T-cell's surface. In addition to T-20, the entry inhibitors PRO-542, SCH-C, SCH-D, and T-1249 may also be used in the compositions and methods described herein.

Turning to the first entry inhibitor discussed above, T-20 is a linear 36 amino acid synthetic peptide having an acetylated N-terminus and a carboxamide group at its C-terminus (*J Virol.* 2001 September; 75(18):8605-14). The molecular weight of T-20 is 4492. T-20 is composed of naturally occurring L-amino acid residues, and possesses the primary amino acid sequence shown below as SEQ ID NO:1:

SEQ ID NO: 1
Acetyl-Tyr-Thr-Ser-Leu-Ile-His-Ser-Leu-Ile-Glu-

Glu-Ser-Gln-Asn-Gln-Gln-Glu-Lys-Asn-Glu-Gln-Glu-

Leu-Leu-Glu-Leu-Asp-Lys-Trp-Ala-Ser-Leu-Trp-Asn-

Trp-Phe-NH$_2$.

Using amino acid abbreviations, SEQ ID NO:1 can alternatively be presented as:
SEQ ID NO:1. YTSLIHSLIEESQNQQEKNEQELLELDKWASLWNWF.

For use in the present invention, the T-20 polypeptide sequence may be blocked and/or derivatized at one or both of its amino or carboxy termini, as described in U.S. Pat. No. 5,464,933, or may possess a blocking group at one or more of the lysine positions. In particular, the tyrosine amino terminus may be blocked or derivatized with an acyl group and the phenylalanine carboxy terminis may be blocked or derivatized with an amino group.

Additional T-20-like sequences contemplated for use in the present invention comprise amino acids 638 to 673 of the HIV-1$_{LAI}$, gp41 protein, and fragments, analogs, and homologs thereof, as described in U.S. Pat. No. 5,464,933, the contents of which are expressly incorporated herein by reference. Particularly preferred peptide sequences correspond to SEQ ID NOs: 1, 3, 4, 5, 6, and 7 as described in U.S. Pat. No. 5,464,933. T-1249 represents another entry inhibitor for use in the present invention.

Similar to T-20, T-1249 is also derived from various retroviral envelope (gp41) protein sequences, but possesses pharmacokinetic properties that are somewhat advantageous over those of T-20. T-1249 is a hybrid polypeptide that contains a core polypeptide sequence linked to an enhancer peptide sequence. T-1249 possesses 39 amino acids and binds to a slightly different region of HIV gp41 than T-20. The amino acid sequence of T-1249 is shown in FIG. 13B of U.S. Pat. No. 6,656,906. T1249 exhibits in vitro activity against HIV-1, HIV-2, and SIV isolates.

Additional exemplary entry inhibitor sequences (similar to those of T-1249) for use in the present invention are described in U.S. Pat. No. 6,656,906, the contents of which are expressly incorporated herein by reference. Particularly preferred sequences are those shown in FIGS. 13 A-C in U.S. Pat. No. 6,656,906. Methods useful for determining the antiviral activity of any of the above hybrid gp-41 derived polypeptide sequences, or the activity of a corresponding polymer conjugate or composition thereof, are also described in U.S. Pat. No. 6,656,906.

Another preferred peptide-based entry inhibitor is PRO-542, a hybrid fusion protein that combines the HIV-binding region of the CD4 receptor with a human antibody molecule. PRO-542 neutralizes HIV by binding to gp120, thereby preventing viral attachment to host cells. More particularly, PRO-542 is a CD4-IgG2 chimeric heterotetramer having a sequence of amino acids as described in U.S. Pat. No. 6,187,748, the contents of which are expressly incorporated herein by reference. Even more specifically, PRO 542 is made up of the N-terminal domains of human CD4 fused to the light and heavy chain constant regions of IgG2. PRO 542 is considered an attachment inhibitor, and acts very early in the viral entry process. Assays such as a syncytium inhibition assay and methods for determining the antiviral properties of such hybrid fusion proteins are described in U.S. Pat. No. 6,187,748, and can be employed by one skilled in the art to similarly determine the antiviral activity of the corresponding polymer conjugates or compositions.

Additional non-limiting examples of peptide-based entry inhibitors for use in the present invention include CCR5 peptides, both sulfonated and non-sulfonated forms thereof, e.g., PRO 140, and PRO 367. Sulfated CCR5 peptides are described in U.S. Patent Application Serial No. 2003/0139571.

PRO 140 (previously referred to as PA14) is a mouse immunoglobulin G1 humanized monoclonal antibody which is classified as a CCR5 coreceptor inhibitor. PRO 140, and anti-CCR5 monoclonal antibody, binds to a complex epitope spanning multiple extracellular domains on CCR5. It potently inhibits CCR5-mediated HIV-1 entry on target cells, namely CD4+ T cells and macrophages, at concentrations that do not prevent CC-chemokine signaling (Trkola, A., et al., *Journal of Virology*, January 2001, Vol. 75, No. 2, 579-588). Preparation, isolation, and purification of PRO 140 is typically carried out as described in Olson, W. C., et al., 1999, *J. Virol.* 73:4145-4155. The monoclonal antibody, PRO 140, also corresponds to ATCC Accession No. HB-12610, as described in Olsen, et al, U.S. Patent Application No. 2004/0228869.

Additional monoclonal antibodies suitable for use in the present invention include antibodies designated as PA8 (ATCC Accession No. HB-12605), PA9 (ATCC Accession No. HB-12606), PA10 (ATCC Accession No. HB-12607), PA11 (ATCC Accession No. HB-12608), and PA12 (ATCC Accession No. HB-12609) as described in Olsen, et al., U.S. Patent Application No. 2004/0228869. These antibodies comprise complementarity determining regions (CDRs) that bind to an epitope of chemokine receptor 5 (CCR5). CCR5 is a chemokine receptor which binds members of the C—C group of chemokines, and whose amino acid sequence comprises that provided in Genbank Accession Number 1705896. The subject epitope comprises consecutive amino acid residues present in i) an N-terminus of CCR5, ii) one of three extracellular loop regions of CCR5, or iii) a combination of (i) and (ii).

Biologically active fragments, deletion variants, substitution variants or addition variants of any of the foregoing that maintain at least some degree of antiretroviral activity can also serve as an antiviral in accordance with the invention. Such compounds can be made recombinantly or using synthetic methods well known in the art.

As stated previously, a reference to any one or more of the above-described drugs, as with all of the drugs or active molecules described herein, where applicable, is meant to encompass any and all enantiomers, mixtures of enantiomers including racemic mixtures, prodrugs, pharmaceutically acceptable salt forms, hydrates (e.g., monohydrates, dihydrates, etc.), different physical forms (e.g., crystalline solids, amorphous solids), metabolites, and the like.

II. B. Broad Spectrum Antibiotic

A broad spectrum antiobiotic for use in the invention is one which possesses activity against a wide range of disease-causing microorganisms (that is to say, is effective in inhibiting growth of a number of microbial pathogens).

In one embodiment, a broad-spectrum antibiotic for use in the invention is one that possesses activity against both gram-positive and gram-negative organisms. Exemplary broad spectrum antibiotics for use in the invention include compounds falling within the following chemical classifications or categories: aminoglycosides, macrolides, ketolides, quinolones, tetracyclines, sulfonamides, and beta-lactams (including the cephalosporins), among others. In yet another embodiment, a broad spectrum antibiotic for use in the invention is one demonstrating a degree of anti-microbial activity comparable to that of any of the herein described aminoglycosides, macrolides, ketolides, quinolones, tetracyclines, sulfonamides, or beta-lactams, in particular, against species falling within four or more different microbial genuses selected from *Actinomyces, Bacillus, Bordetella, Borrelia, Campylobacter, Chlamydia, Clostridium, Corynebacterium, Cryptosporidium, Entamoeba, Enterobacter, Escherichia, Gardnerella, Haemophilus, Klebsiella, Legionella, Leishmania, Moraxella, Mycobacterium, Mycoplasma, Neisseria, Nocardia, Proteus, Providencia, Pseudomonas, Salmonella, Serpulina, Serratia, Shigella, Staphylococcus, Streptococcus, Toxoplasmosis, Treponem*, and *Tubercle*.

As stated previously, one of the heretofore unrecognized advantages of the invention is the combination of drugs from any two and preferably from each of the following drug classes: (i) an antiviral compound, (ii) a broad-spectrum antibiotic, and (iii) an anti-protozoal compound, to provide a mixture effective in the treatment of certain inflammatory conditions such as reactive arthritis and osteoarthritis, as demonstrated in the accompanying Examples.

TETRACYCLINES. The first type of broad spectrum antibiotic for use in the invention, the tetracyclines, belongs to a class that shares a four-membered ring structure composed of four fused 6-membered (hexacyclic) rings. The tetracyclines exhibit their activity by inhibiting the binding of the aminoacyl tRNA to the 30S ribosomal subunit in susceptible bacteria. Tetracyclines for use in the invention include chlortetracycline, demeclocycline, doxycycline, minocycline, oxytetracycline, chlortetracycline, methacycline, mecocycline, tigecycline, and tetracycline. The tetracyclines are effective against many known organisms including α-hemolytic streptococci, nonhemolytic streptococci, gram-negative bacilli, rickettsiae, spirochetes, *Mycoplasma*, and *Chlamydia*.

One particularly preferred tetracycline for use in the invention is tetracycline. Tetracycline is effective against microbes such as the following: *Rickettsiae, Mycoplasma pneumoniae, Borrelia recurrentis, Haemophilus ducreyi* (chancroid), *Pasteurella pestis, Pasteurella tularensis, Bartonella bacilliformis, Bacteroides* species, *Vibrio comma, Vibrio fetus, Brucella* species, *Escherichia coli, Enterobacter aerogenes* (formerly *Aerobacter aerogenes*), *Shigella* species, *Mima* species, *Herellea* species, *Haemophilus influenzae*, and *Klebsiella* species. Additionally, tetracycline possesses activity against pathogens such as *Neisseria gonorrhoeae, Treponema pallidum, Treponema pertenue, Listeria monocytogenes, Clostridium* species, *Bacillus anthracis, Fusobacterium fusiforme, Actinomyces* species, and *Chlamydia trachomati*.

The tetracycline derivative, oxytetracycline, possesses a spectrum of activity similar to tetracycline, and is also useful in the compositions and methods of the invention. Oxytetracycline possesses activity against the following: Rickettsiae, *Mycoplasma pneumoniae, Borrelia recurrentis), Haemophilus ducreyi* (chancroid), *Pasteurella pestis, Pasteurella tularensis, Bartonella bacilliformis, Bacteroides* species, *Vibrio comma* and *Vibrio fetus, Brucella* species, *Escherichia coli, Enterobacter aerogenes* (formerly *Aerobacter aerogenes*), *Shigella* species, *Mima* species and *Herellea* species, *Haemophilus influenzae* (respiratory infections), *Klebsiella* species, *Diplococcus pneumoniae, Staphylococcus aureus, Neisseria gonorrhoeae, Treponema pallidum, Treponema pertenue, Listeria monocytogenes, Clostridium* species, *Bacillus anthracis, Fusobacterium fusiforme*, and *Actinomyces* species.

Other tetracyclines for use in the invention, i.e., demeclocycline, doxycycline, minocycline, chlortetracycline, methacycline, tigecycline, and meclocycline, all exhibit antimicrobial spectra similar to tetracycline or oxytetracline as described in detail above. Tigecycline, a broad spectrum glycylcycline antibiotic, has activity against a broad range of Gram-positive, Gram-negative, atypical anaerobic and other antibiotic-resistant bacteria, and possesses more potent activity against tetracycline-resistant organisms (Nathwani, D., *Int J. Antimicrob Agents*. 2005 March, 25(3): 185-92).

One particularly preferred tetracycline for use in the invention is Minocycline. Minocycline, also referred to as, 4S-(4a, 4aa,5aa,12aa)]-4,7-bis(dimethylamino)-1,4,4a,5,5a,6,11, 12a-octahydro-3,10,12,12a-tetrahydroxy-1,11-dioxo-2- naphthacenecarboxamide monohydrochloride, commercially available as the hydrochloride salt, is a semi-synthetic tetracycline derivative that has a spectrum of antibacterial activity that is similar to tetracycline. It is active against streptococci, enterobacteria, and some mycobacteria, and also against such species as *Staphylococcus aureus, Neisseria meningitides, Acinetobbacter, Bacteroides, Haemophilus*, and *Nocardia*.

AMINOGLYCOSIDES. Another type of broad-spectrum antibiotic for use in the invention is the aminoglycosides. Aminoglycosides are compounds derived from species of *Streptomyces* or *Micomonospora* bacteria and are primarily used to treat infections caused by gram-negative bacteria. Drugs belonging to this class all possess the same basic chemical structure, i.e., a central hexose or diaminohexose molecule to which two or more amino sugars are attached by a glycosidic bond. The aminoglycosides are bactericidal antibiotics that bind to the 30S ribosome and inhibit bacterial protein synthesis. They are active primarily against aerobic gram-negative bacilli and staphylococci.

Aminoglycoside antibiotics for use in the invention include amikacin (Amikin®), gentamicin (Garamycin®), kanamycin (Kantrex®), neomycin (Mycifradin®), netilmicin (Netromycin®), paromomycin (Humatin®), streptomycin, and tobramycin (TOBI Solution®, TobraDex®). With the exception of streptomycin, which has a more limited antibiotic spectrum, the aminoglycosides exhibit activity against gram-negative aerobic bacilli but typically lack activity against streptococci and anaerobes.

As stated above, an antibiotic for use in the invention is a broad-spectrum antibiotic. For instance, amikacin is effective in the treatment of serious nosocomial gram-negative bacterial infections and mycobacterial infections in AIDS patients. Gentamicin and tobramycin are effective in the treatment of pneumonia and meningitis caused by gram-negative bacilli and in the treatment of gram-positive nosocomial bacterial infections. Yet another aminoglycoside, kanamycin, is effective against organisms such as *Staphylococcus aureus* (including penicillinase-producing strains), *Staph. epidermidis, Neisseria gonorrhoeae, Haemophilus influenzae, Escherichia coli, Enterobacter, Shigella, Salmonella, Klebsiella pneumoniae, Serratia, Providencia*, and many strains of *Proteus*. Neomycin, a mixture of neomycin A, B and C (where each of the neomycins differ in the side chains attached to the amino sugars), is effective against *Enterobacter, Salmonella* and *Shigella*. Further, netilmicin is highly active against most Gram-negative and some Gram-postive organisms, including some which are resistant to other aminoglycosides. Specifically, netilmicin is active against 85% of strains of *pseudomonas aeruginosa*, methicillin-resistant strains of *Staph. aureus* and *Proteus*. Streptomycin is active against both gram-positive and gram-negative bacteria including species resistant to other antibiotics, e.g., some streptococci, penicillin-resistant staphylococci, and bacteria of the genera *Proteus* and *Pseudomonas*, and is also effective against tubercle bacilli.

Paromomycin is yet another aminoglycoside, but is typically used for the treatment of non-bacterial organisms such as parasites, leishmaniasis, and cryptosporidiosis. When administered orally, paromomycin is effective in the treatment of giardiasis, amebiasis (*Entamoeba hystolytica*) and cryptosporidiosis (*Cryptosporidium parvum*). When administered topically, paromomycin is effective in the treatment of Old World cutaneous leishmaniasis (*Leishmania major, L. tropica, L. aethopica*.

Aminoglycosides such as the foregoing are particularly useful when employed in the compositions and methods of the invention.

MACROLIDES. Yet another type of broad-spectrum antibiotic for use in the invention is a macrolide. The macrolides are a group of polyketide antibiotic drugs whose activity stems from the presence of a macrolide ring (a large 14-, 15-, or 16-membered lactone ring) to which one or more deoxy sugars, usually cladinose and desosamine, are attached. Macrolides are primarily bacteriostatic and bind to the 50S subunit of the ribosome, thereby inhibiting bacterial synthesis. Macrolides are active against aerobic and anaerobic gram-positive cocci (with the exception of enterococci) and against gram-negative anaerobes.

Macrolides for use in the invention include azithromycin (Zithromax®), clarithromycin (Biaxin®), dirithromycin (Dynabac®), erythromycin, clindamycin, and lincomycin.

The macrolide, erythromycin, is effective against the following pathogens: *Chlamydia pneumoniae, Chlamydia trachomatis, Legionella pneumophilia, mycoplasma pneumoniae, Bordetella pertussis, Corynebacterium diphtheriae*, and *Campylobacter jejuni*. Erythromycin is also effective against *ureaplasma urealyticum, Treponema pallidum, Staphylococcus, Streptococcus, Bacillus anthracis*, and *Clostridium* species.

The macrolide antibiotic, azithromycin, is effective against pathogens such as *Haemophilus Influenzae, Moraxella catarrhalis, Toxoplasmosis gondii, Mycobacterium Avium Complex*, and *Borrelia Burgdorferi*.

The macrolide, clarithromycin, also suitable for use in the invention, along with antibiotics having a similar spectrum of activity, is effective against pathogens such as *Streptococcus Pneumoniae, Staphylococcus aureas, Toxoplasmosis gondii, Mycobacterium leprae, Mycobacterium Avium Complex*, and *Borrelia Burgdorferi*.

Dirithromycin is a yet another broad spectrum antibiotic for use in the invention. Dirithromycin is effective against pathogens such as *Haemophilus influenzae, Moraxella catarrhalis, Streptococcus pneumoniae, Legionella pneumophila, Mycoplasma pneumoniae*, and *Streptococcus pyogenes*.

Clindamycin has antibacterial activity against sensitive gram-positive organisms; its spectrum of activity is similar to that of erythromycin. Clindamycin possesses activity against staphylococci (including penicillinase-producing and methicillin resistant strains), hemolytic streptococci, *S. viridans* and *S. pneumoniae*. In addition, some strains of *C. tetani, C. perfringens, C. diphtheriae, P. acnes, A. israelii, H. influenzae, N. gonorrheae* and *C. trachomatis* are sensitive in vitro. Moreover, clindamycin has demonstrated activity against pathogens responsible for bacterial vaginosis, i.e., *Haemophilus, Gardnerella*, and *Corynebacterium*.

Yet another broad-spectrum antibiotic for use in the invention is lincomycin. Lincomycin is active primarily against gram-positive bacteria such as: *Staphylococcus* sp., *Streptococcus* sp., *Clostridium* sp., *Bacillus anthracis* and *Corynebacterium* sp. It is also active against some gram-negative bacteria of the species *Bordetella, Actinobacillus, Nocardia* and *Actinomyces*, and is particularly effective against *Serpulina hyodysenteriae, Mycoplasma hyopneumoniae* and *Mycoplasma gallisepticum*.

KETOLIDES. Also suitable for use in the present invention are the ketolides, another type of broad-spectrum antibiotic. The ketolides belong to a new class of semi-synthetic 14-membered ring macrolides in which the erythromycin macrolactone ring structure and the D-desosamine sugar attached at position 5 are retained, however, replacing the L-cladinose moiety and hydroxyl group at position 3 is a 3-keto functional group. The ketolides bind to the 23S rRNA, and their mechanism of action is similar to that of macrolides (Zhanel, G. G., et al., *Drugs,* 2001; 61(4):443-98). The ketolides exhibit good activity against gram-positive aerobes and some gram-negative aerobes, and possess excellent activity against *Streptococcus* spp. including mefA and ermB-producing *Streptococcus pneumoniae,* and *Haemophilus influenzae.* Representative ketolides for use in the invention include telithromycin (formerly known as HMR-3647), HMR 3004, HMR 3647, cethromycin, EDP-420, and ABT-773.

QUINOLONES. Yet another type of broad-spectrum antibiotic for use in the invention is the quinolone class. Structurally, the quinonolones possess a 1,4 dihydro-4-oxo-quinolinyl moiety bearing an essential carboxyl group at position 3. Functionally, the quinolones inhibit prokaryotic type II topoisomerases, namely DNA gyrase and, in a few cases, topoisomerase IV, through direct binding to the bacterial chromosome.

Quinolones for use in the invention span first, second, third and fourth generation quinolones, including fluoroquinolones. Such compounds include nalidixic acid, cinoxacin, oxolinic acid, flumequine, pipemidic acid, rosoxacin, norfloxacin, lomefloxacin, ofloxacin, enrofloxacin, ciprofloxacin, enoxacin, amifloxacin, fleroxacin, gatifloxacin, gemifloxacin, clinafloxacin, sitafloxacin, pefloxacin, rufloxacin, sparfloxacin, temafloxacin, tosufloxacin, grepafloxacin, levofloxacin, moxifloxacin, and trovafloxacin. Additional quinolones suitable for use in the invention include those described in Hooper, D., and Rubinstein, E., "*Quinolone Antimicrobial Agents, 3$^{rd}$ Edition*", American Society of Microbiology Press, Washington D.C. (2004).

First generation quinolones for use in the invention include nalidixic acid (NegGram®) and cinoxacin (Cinobac®). Nalidixic acid is effective against the majority of *E. Coli, Enterobacter, Klebsiella,* and *Proteus* species, while cinoxacin is effective against *Escherichia coli, Proteus mirabilis, Proteus vulgaris, Klebsiella* species (including *K. pneumoniae*), and *Enterobacter* species.

Second generation quinolones for use in the invention include ciprofloxacin (Cipro®), ofloxacin (Floxin®), enoxacin (Penetrex®), lomefloxacin (Maxaquin®), and norfloxacin (Noroxin®). Generally, second generation quinolones are effective against gram negative organisims including *Pseudomonas* and some gram-positive organisms such as *Staphylococcus.* A preferred quinolone for use in the invention is ciprofloxacin. Ciprofloxacin (cipro) is effective against numerous gram positive and gram negative bacteria. Specifically, ciprofloxacin is effective against: Aerobic gram positive microbes including *Enterococcus faecalis; Staph Aureus; Staph epidermis; Staph saprophyticus; Strep pneumoniae;* and *Strep pyogenes*; Aerobic gram negative microbes including *Campylobacter jejuni, Citrobacter diversus, Citrobacter freundii, Enterobacter cloacae, E. Coli, Haemophilus influenzae, Haemophilus parainfluenzae, Klebsiella pneumonae, Morganella morganii, Neisseria gonorrheae, Proteum mirabilis, Proteus vulgaris, Providencia rettgeri, Providencia stuartii, Pseudomonas aeruginose, Salmonella typhi, Serratia marcescens, Shigella flexneri,* and *Shigella sonnei.* Moreover, cipro is effective against 90% of the strains of the following in vitro: *Staph haemolyticus, Staph hominis* and *Acinetobacter Iwoffi, Aeromonas caviae Aeromonas hydrophilia, Brucella melitensis, Campylobacter coli, Edwardsiella tarda, Haemophilus ducreyi Klebsiella oxytoca, Legionella pneumophila, Moraxella catarrhalis, Neisseria meningitides, Pasteurella multocida Salmonella enteritidis, Vibrio cholerae, Vibrio parahaemolyticus, Vibrio vulnificus* and *Yersinia enterocolitica.* Cipro is also moderately effective against *Clamydia trachomatis* and *Mycobacterium tuberculosis.*

Another second generation quinolone, norfloxacin, is effective against the following pathogens: *Enterococcus faecalis, Escherichia coli, Klebsiella pneumoniae, Proteus mirabilis, Pseudomonas aeruginosa, Staphylococcus epidermidis, Staphylococcus saprophyticus, Citrobacter freundii, Enterobacter aerogenes, Enterobacter cloacae, Proteus vulgaris, Staphylococcus aureus, Streptococcus agalactiae, Neisseria gonorrhoeae,* and *Serratia marcescens.*

Microbial strains susceptible to lomefloxacin, a second generation difluoroquinolone, include the following: *Escherichia coli, Klebsiella pneumoniae, Proteus mirabilis, Staphylococcus saprophyticus, Citrobacter diversus, Enterobacter cloacae, Escherichia coli, Pseudomonas aeruginosa, Branhamella catarrhalis,* and *Haemophilus influenzae.*

Yet another second generation quinolone for use in the invention includes enoxacin. Enoxacin is effective against the following microbial pathogens: *Escherichia coli, Staphylococcus epidermidis, Staphylococcus saprophyticus, Klebsiella pneumoniae, Proteus mirabilis, Pseudomonas aeruginosa,* and *Enterobacter cloacae.*

Ofloxacin, yet an additional second generation quinolone for use in the invention, possesses activity against microbes such as *Haemophilus influenzae, Streptococcus pneumoniae, Staphylococcus aureus, Streptococcus pyogenes, Proteus mirabilis, Neisseria gonorrhoeae,* and *Chlamydia trachomatis.*

Third generation quinonolones possess an expanded spectrum of activity when compared to first and second generation quinolones. Third generation quinolones for use in the invention include levofloxacin (Levaquin®), sparfloxacin (Zagam®), gatifloxacin (Tequin®), and moxifloxacin (Avelox®). The third generation quinolones generally possess the same spectrum of antimicrobial activity as the second generation agents, in addition to having expanded activity against gram positive and atypical pathogens.

For instance, microbes susceptible to levofloxacin include *Streptococcus pneumoniae, Haemophilus influenzae, Moraxella catarrhalis, Staphylococcus aureus, Haemophilus parainfluenzae, Pseudomonas aeruginosa, Serratia marcescens, Escherichia coli, Klebsiella pneumoniae, Chlamydia pneumoniae, Legionella pneumophila,* and *Mycoplasma pneumoniae, Enterococcus faecalis, Streptococcus pyogenes, Proteus mirabilis, Staphylococcus epidermidis, Enterobacter cloacae,* and *Staphylococcus saprophyticus.*

Similar in activity to levofloxacin, sparfloxacin, yet another quinolone for use in the invention, is active against *Chlamydia pneumoniae, Haemophilus influenzae, Haemophilus parainfluenzae, Moraxella catarrhalis, Mycoplasma pneumoniae, Streptococcus pneumoniae, Enerobacter cloacae, Klebsiella pneumoniae, Staphylococcus aureus* and *Streptococcus pneumonia.* The third generation quinolone, gatifloxacin, is similarly effective against *Streptococcus pneumoniae, Haemophilus influenzae, Haemophilus parainfluenzae, Moraxella catarrhalis, Staphylococcus aureus, Mycoplasma pneumoniae, Chlamydia pneumoniae, Legionella pneumophila,* and *Streptococcus pyogenes,* while moxifloxacin is effective against *Streptococcus pneumoniae, Haemophilus influenzae, Moraxella catarrhalis, Haemophilus parainfluenzae, Klebsiella pneumoniae, Staphylococcus aureus, Mycoplasma pneumoniae, Chlamydia pneumoniae,* and *Streptococcus pyogenes.*

Fourth generation quinolones are also suitable for use in the invention. Fourth generation quinolones have an expanded spectrum of activity similar to the third generation agents, in addition to broad anaerobic coverage. For example, the agent, trovafloxacin, has been shown to be active againt most strains of the following, both in vitro and in clinical infections in vivo: *Enterococcus faecalis, Staphylococcus aureus* (methicillin-susceptible strains), *Streptococcus agalactiae, Streptococcus pneumoniae* (penicillin-susceptible strains), *Viridans* group streptococci, *Escherichia coli, Gardnerella vaginalis, Haemophilus influenzae, Klebsiella pneumoniae, Moraxella catarrhalis, Proteus mirabilis, Pseudomonas aeruginosa, Bacteroides fragilis, Peptostreptococcus* species, *Prevotella* species, *Chlamydia pneumoniae, Legionella pneumophila*, and *Mycoplasma pneumoniae*. Additional fourth generation quinolones include clinafloxacin and sitafloxacin.

SULFONAMIDES. A broad spectrum antibiotic for use in the invention may also be a sulfonamide. Drugs belonging to the sulfonamide class all possess a sulfonamide moiety, —$SO_2NH_2$, or a substituted sulfonamide moiety, where one of the hydrogens on the nitrogen is replaced by an organic substituent. Illustrative N-substituents include substituted or unsubstituted thiazole, pyrimidine, isoxazole, and other functional groups. Sulfonamide antiobiotics all share a common structural feature, i.e., they are all benzene sulfonamides, meaning that the sulfonamide functionality is directly attached to a benzene ring. The structure of sulfonamide antibiotics is similar to p-aminobenzoic acid (PABA), a compound that is needed in bacteria as a substrate for the enzyme, dihydroptroate synthetase, for the synthesis of tetrahydrofolic acid. The sulfonamides function as antibiotics by interfering with the metabolic processes in bacteria that require PABA, thereby inhibiting bacterial growth and activity.

Sulfonamide antibiotics for use in the invention include the following: mafenide, phtalylsulfathiazole, succinylsulfathiazole, sulfacetamide, sulfadiazine, sulfadoxine, sulfamazone, sulfamethazine, sulfamethoxazole, sulfametopirazine, sulfametoxypiridazine, sulfametrol, sulfamonomethoxine, sulfamylon, sulfanilamide, sulfaquinoxaline, sulfasalazine, sulfathiazole, sulfisoxazole, sulfisoxazole diolamine, and sulfaguanidine.

The sulfonamides differ mostly in the relative potency of their antimicrobial effect, but the spectrum of action for the different drugs is similar. These drugs can inhibit both gram-positive and gram-negative bacteria including some enterics, *Nocardia, Chlamydia trachomatis* and some protozoa. Generally, *Pseudomonas, Serratia*, and *Proteus* are not inhibited. An exception is Mafenide (Sulfamylon™), sold commercially as a monoacetate salt, which has a mechanism of action that is different from that of typical sulfonamides. Mafenide is not antagonized by pABA, serum, pus or tissue exudates, and there is no correlation between bacterial sensitivities to mafenide and to the other sulfonamides. Mafenide exerts broad bacteriostatic action against many gram-negative and gram-positive organisms, including *Pseudomonas aeruginosa* and certain strains of anaerobes.

BETA-LACTAMS. Also suitable for use in the invention are the broad spectrum antibiotics classified structurally as beta-lactams. All members of this broad spectrum antibiotic class possess a beta-lactam ring and a carboxyl group, resulting in similarities in both their pharmacokinetics and mechanism of action. The majority of clinically useful beta-lactams belong to either the penicillin group or the cephalosporin group, including cefamycins and oxacephems. The beta-lactams also include the carbapenems and monobactams.

Generally speaking, beta-lactams inhibit bacterial cell wall synthesis. More specifically, these antibiotics cause 'nicks' in the peptidoglycan net of the cell wall that allow the bacterial protoplasm to flow from its protective net into the surrounding hypotonic medium. Fluid then accumulates in the naked protoplast (a cell devoid of its wall), and it eventually bursts, leading to death of the organism. Mechanistically, beta-lactams act by inhibiting D-alanyl-D-alanine transpeptidase activity by forming stable esters with the carboxyl of the open lactam ring attached to the hydroxyl group of the enzyme target site. Beta-lactams are extremely effective and typically are of low toxicity.

As a group, these drugs are active against many gram-positive, gram-negative and anaerobic organisms.

Drugs falling into this category include 2-(3-alanyl)clavam, 2-hydroxymethylclavam, 7-methoxycephalosporin, epi-thienamycin, acetyl-thienamycin, amoxicillin, apalcillin, aspoxicillin, azidocillin, azlocillin, aztreonam, bacampicillin, blapenem, carbenicillin, carfecillin, carindacillin, carpetimycin A and B, cefacetril, cefaclor, cefadroxil, cefalexin, cefaloglycin, cefaloridine, cefalotin, cefamandole, cefapirin, cefatrizine, cefazedone, cefazolin, cefbuperazone, cefcapene, cefdinir, cefditoren, cefepime, cefetamet, cefixime, cefinenoxime, cefinetazole, cefminox, cefmolexin, cefodizime, cefonicid, cefoperazone, ceforamide, cefoselis, cefotaxime, cefotetan, cefotiam, cefoxitin, cefozopran, cefpiramide, cefpirome, cefpodoxime, cefprozil, cefquinome, cefradine, cefroxadine, cefsulodin, ceftazidime, cefteram, ceftezole, ceftibuten, ceftizoxime, ceftriaxone, cefuroxime, cephalosporin C, cephamycin A, cephamycin C, cephalothin, chitinovorin A, chitinovorin B, chitinovorin C, ciclacillin, clavulanate salt, clavulanic acid, clometocillin, cloxacillin, cycloserine, deoxy pluracidomycin B and C, dicloxacillin, dihydro pluracidomycin C, epicillin, epithienamycin D, E, and F, ertapenem, faropenem, flomoxef, flucloxacillin, hetacillin, imipenem, lenampicillin, loracarbef, mecillinam, meropenem, metampicillin, meticillin (also referred to as methicillin), mezlocillin, moxalactam, nafcillin, northienamycin, oxacillin, panipenem, penamecillin, penicillin G, N, and V, phenethicillin, piperacillin, povampicillin, pivcefalexin, povmecillinam, prvmecillinam, pluracidomycin B, C, and D, propicillin, sarmoxicillin, sulbactam, sultamicillin, talampicillin, temocillin, terconazole, thienamycin, and ticarcillin.

Preferred beta lactams include ampicillin, amoxicillin, penicillin V, imipenem, cloxacillin, dicloxacillin, nafcillin, oxacillin, bacampicillin, carbenicillin, cefadroxil, cephalexin, cephradine, ceflaclor, cefprozil, cefuroxime, loracarbef, cefdinir, cefixime, cefpodoxime, ceftibuten, and meropenem.

In terms of antimicrobial spectrum, penicillin V is active against *Streptococcus* and oral cavity anaerobes. Cloxacillin, dicloxacillin, nafcillin, and oxacillin are effective against *Staphylococcus aurreus* and *Streptococcus* species. Amoxicillin, ampicillin and bacampicillin exhibit activity against *Streptococcus* and oral cavity anaerobes, in addition to *Listeria monocytogenes, Enterococcus* species, *Proteus mirabilis* and some strains of *Escherichia coli*. Carbenicillin is active against *Pseudomonas* and *Klebsiella*. The cephalosporins, cefadroxil, cephalexin and cephradine are active against *S. aureus, E. coli, P. mirabilis* and *Klebsiella*. The second-generation cephalosporins, cefaclor, ceclor, cefprozil, and cefuroxime, in addition to loracarbef, exhibit activity against *S. aureus, H. influenzae, M. catarrhalis, E. coli, P. mirabilis*, and *Klebsiella*. The third generation cephalosporins, cefdinir, cefixime, cefpodoxime, and ceftibuten exhibit somewhat expanded coverage of gram-negative organisms, in addition to enhanced coverage of *Proteus vulgaris* and *Providencia*.

II. C. Anti-Protozoal Compound

The compositions and methods of the invention may, in certain embodiments, employ an anti-protozoal compound. An anti-protozoal compound is one that destroys protozoa or inhibits their growth and ability to reproduce. Drugs that function as anti-protozoal agents may also, in certain instances, be anti-bacterial in nature, particularly against anaerobic pathogens. Exemplary protozoa of medical importance include *Plasmodium* (the cause of malaria), *Entamoeba histolytica* (the cause of amebiasis, amebic dysentery), *Trichomonas vaginalis* (a cause of vaginal infection), and *Pneumocystis carinii* (a common cause of pneumonia in immuno-deficient patients).

Anti-protozoal compounds for use in the invention include chloroquine, pyrimethamine, mefloquine, hydroxychloroquine; metronidazole, atovaquone, eflornithine, furazolidone, iodoquinol, pentamidine, pyrimethamine-sulfonamide, trimethoprim-sulfamethoxazole, halofantrine, artesunate, artelenic acid, [8-(6-diethylaminohexylamino)-6-methoxy-4-methylquinoline dihydrochloride] and [8-[(4-amino-1-methylbutyl)amino]-2,6-dimethoxy-4-methyl-5-(3-trifluoromethylphenoxy-7)quinoline succinate], nitazoxamide, among others.

Preferred anti-protozoals include the nitroimidazole compound, metronidazole (Flagyl®), nitazoxamide, eflornithine (Ornidyl®), furazolidone (Furoxone®), hydroxychloroquine (Plaquenil®), iodoquinol (Diquinol®, Yodoquinol®, Yodoxin®), and pentamidine (Pentam 300®).

One particularly preferred anti-protozoal is metronidazole, 2-methyl-5-nitroimidazole-1-ethanol. Metronidazole is amebicidal, trichomonacidal, and bactericidal. A chemically reactive, reduced form of the drug is thought to be responsible for its activity, and its spectrum of activity includes the following: anaerobic gram-negative bacilli including most *Bacteroides* species, *Fusobacterium* and *Veillonella*; anaerobic gram-positive cocci including *Clostridium*, *Eubacterium*, *Peptococcus*, and *Peptostreptococcus*, *H. pylori*, *G. vaginalis*, *E. histolytica*, *T. vaginalis*, and *G. lamblia*.

II. D. Exemplary Anti-Microbial Combinations

As described previously, compositions and combinations of the invention include at least two of, and preferably include each of (i) an antiviral, (ii) a broad-spectrum antibiotic, and (iii) an anti-protozoal compound. Any of the herein described compounds from each of the above classes, when used in combination as described herein, is suitable for use in treating reactive arthritis, osteoarthritis, bursitis, and the like.

For instance, in referring to Table 1 below, an anti-inflammatory combination of the invention comprises, in one embodiment, a compound from column I and a compound from column II. Alternatively, in another embodiment, a combination of the invention comprises a compound from column I and column III, or a compound from column II and a compound from column III. Referring now to particular subclasses of compounds, illustrative combinations in accordance with the invention comprise the following types of compounds. For example, for combinations comprising a compound from column I and a compound from column II, representative combinations include (I)-(II): NA-AG, NA-MCL, NA-QNL, NA-TC, NA-SA, and NA-BL, RTI-AG, RTI-MCL, RTI-QNL, RTI-TC, RTI-SA, and RTI-BL, PI-AG, PI-MCL, PI-QNL, PI-TC, PI-TC, PI-SA, PI-BL, EI-AG, EI-MCL, EI-QNL, EI-TC, EI-SA, EI-BL, O-AG, O-MCL, O-QNL, O-TC, O-SA, O-BL, where abbreviations for each of the sub-classes correspond to those in Table I below. Additional exemplary combinations include each of the foregoing combined with an anti-protozoal (AP). Additional combinations, e.g., comprising a compound from column I and a compound from column III include NA-AP, RTI-AP, PI-AP, EI-AP, O-AP. Further combinations comprise, e.g., a compound from column II and a compound from column III, AG-AP, MCL-AP, QNL-AP, TC-AP, SA-AP, and BL-AP. A particularly preferred combination of the invention is one comprising a NA, a TC, and an AP.

TABLE 1

ANTI-MICROBIAL COMBINATIONS FOR TREATING INFLAMMATORY CONDITIONS

| ANTIVIRAL (AV) (I) | BROAD SPECTRUM ANTIBIOTIC (BSA) (II) | ANTI-PROTOZOAL (AP) (III) |
|---|---|---|
| A. Nucleoside Analog (purine based or thymidine based), NA. | F. Aminoglycoside, AG | No additional sub-classes |
| B. Reverse Transcriptase Inhibitor, RTI | G. Macrolide, MCL | |
| C. Protease Inhibitor, PI | H. Ketolide, KT | |
| D. Entry Inhibitor, EI | I. Quinolone, QNL | |
| E. Other, O | J. Tetracycline, TC | |
| | K. Sulfonamide, SA | |
| | L. Beta-lactam, BL | |

Illustrative compounds falling within each of the categories in Table I are presented in Table 2. One or more of each of the particular compounds can be substituted in the class-based combinations provided above to provide an anti-inflammatory, e.g., an anti-reactive arthritis or osteoarthritis, combination of the invention.

TABLE 2

ANTIMICROBIAL COMBINATION: REPRESENTATIVE COMPOUND COMPONENTS

| ANTIVIRAL COMPOUND (AV) | BROAD-SPECTRUM ANTIBIOTIC (BSA) | ANTI-PROTOZOAL (AP) |
|---|---|---|
| NA: acyclovir, gancyclovir, pencyclovir, idoxuridine, trifluridine, brivudin, adenosine arabinoside, famcyclovir, valacyclovir, valgancyclovir, dideoxyinosine, adefovir, adefovir dipivoxil, tenofovir, tenofovir disoproxil, cidofovir, zidovudine, lamivudine, stavudine, zalcitibine, emivirine, dianosine, abacavir, emtricitabine, among others | TCL: demeclocycline, doxycycline, minocycline, oxytetracycline, chlortetracycline, meocycline, tetracycline, methacycline, tigecycline, among others | AP: chloroquine, pyrimethamine, mefloquine, hydroxychloroquine; metronidazole, nitazoxamide, atovaquone, eflornithine, furazolidone, iodoquinol, pentamidine, pyrimethamine-sulfonamide, trimethoprim-sulfamethoxazole, halofantrine, artesunate, artelenic acid, [8-(6-diethylaminohexylamino)-6-methoxy-4-methylquinoline dihydrochloride] and [8-[(4-amino-1-methylbutyl)amino]-2,6-dimethoxy-4-methyl-5-(3-trifluoromethylphenoxy-7)quinoline succinate] |

TABLE 2-continued

ANTIMICROBIAL COMBINATION: REPRESENTATIVE COMPOUND COMPONENTS

| ANTIVIRAL COMPOUND (AV) | BROAD-SPECTRUM ANTIBIOTIC (BSA) | ANTI-PROTOZOAL (AP) |
|---|---|---|
| RTI: tivirapine, nevirapine, dipyidodiazepinone, efavirenz, delavirdine, capravirine, among others | MCL: azithromycin, clarithromycin, dirithromycin, erythromycin, clindamycin, lincomycin, among others | |
| PI: saquinavir, ritonavir, indinavir, nelfinavir, amprenavir, lopinavir, atazanavir, among others | QNL: nalidixic acid, cinoxacin, oxolinic acid, flumequine, pipemidic acid, rosoxacin, norfloxacin, clinafloxacin, sitafloxacin, lomefloxacin, ofloxacin, enrofloxacin, ciprofloxacin, enoxacin, amifloxacin, fleroxacin, gatifloxacin, gemifloxacin, pefloxacin, rufloxacin, sparfloxacin, temafloxacin, tosulfoxacin, grepafloxacin, levofloxacin, moxifloxacin, trovafloxacin, among others | |
| EI: T-20, PRO-542, SCH-C, SCH-D, T-1249, PRO140, PRO 367, among others | AG: amikacin, gentamicin, tobramycin, kanamycin, neomycin, netilmicin, paromomycin, streptomycin, among others | |
| O: amantadine, rimantadine, Neu-5Ac2en, anamivir, oseltamivir, methisazone | SA: mafenide, phtalylsulfathiazole, succinylsulfathiazole, sulfacetamide, sulfadiazine, sulfadoxine, sulfamazone, sulfamethazine, sulfamethoxazole, sulfametopirazine, sulfametoxypiridazine, sulfametrol, sulfamonomethoxine, sulfamylon, sulfanilamide, sulfaquinoxaline, sulfasalazine, sulfathiazole, sulfisoxazole, sulfisoxazole diolamine, sulfaquanidine, among others | |
| | BL: 2-(3-alanyl)clavam, 2-hydroxymethylclavam, 7-methoxycephalosporin, epi-thienamycin, acetyl-thienamycin, amoxicillin, apalcillin, aspoxicillin, azidocillin, azlocillin, aztreonam, bacampicillin, blapenem, carbenicillin, carfecillin, cephalothin, carindacillin, carpetimycin A and B, cefacetril, cefaclor, cefadroxil, cefalexin, cefaloglycin, cefaloridine, cefalotin, cefamandole, cefapirin, cefatrizine, cefazedone, cefazolin, cefbuperazone, cefcapene, cefdinir, cefditoren, cefepime, cefetamet, cefixime, cefmenoxime, cefmetazole, cefminox, cefmolexin, cefodizime, cefonicid, cefoperazone, ceforanide, cefoselis, cefotaxime, cefotetan, cefotiam, cefoxitin, cefozopran, cefpiramide, cefpirome, cefpodoxime, cefprozil, cefquinome, cefradine, cefroxadine, cefsulodin, ceftazidime, cefteram, ceftezole, ceftibuten, ceftizoxime, ceftriaxone, cefuroxime, cephalosporin C, cephamycin A, cephamycin C, chitinovorin A, chitinovorin B, chitinovorin C, ciclacillin, clavulanate salt, clavulanic acid, clometocillin, cloxacillin, cycloserine, deoxy pluracidomycin B and C, dicloxacillin, dihydro pluracidomycin C, epicillin, epithienamycin D, E, and F, ertapenem, faropenem, flomoxef, flucloxacillin, hetacillin, imipenem, lenampicillin, loracarbef, mecillinam, meropenem, | |

TABLE 2-continued

ANTIMICROBIAL COMBINATION: REPRESENTATIVE COMPOUND COMPONENTS

| ANTIVIRAL COMPOUND (AV) | BROAD-SPECTRUM ANTIBIOTIC (BSA) | ANTI-PROTOZOAL (AP) |
|---|---|---|
| | metampicillin, meticillin, mezlocillin, moxalactam, nafcillin, northienamycin, oxacillin, panipenem, penamecillin, penicillin G, N, and V, phenethicillin, piperacillin, povampicillin, pivcefalexin, povmecillinam, prvmecillinam, pluracidomycin B, C, and D, propicillin, sarmoxicillin, sulbactam, sultamicillin, talampicillin, temocillin, terconazole, thienamycin, and ticarcillin KT: telithromycin, HMR 3004, HMR 3647, cethromycin, EDP-420, and ABT-773. | |

Particularly preferred combinations of medicaments include the following. One particularly preferred combination of medicaments is valacyclovir or acyclovir, minocycline and metronidazole. Illustrative examples employing at least this combination include Example 8, Example 9, Example 10, Example 11, Example 12, and Example 13. As can be seen, the combination of the invention is effective to significantly diminish, and in some instances, completely resolve or put into remission, all reactive arthritis or osteoarthritis-related symptoms.

As can be seen most effectively in Example 13, osteoarthritic patients who were administered a combination of minocycline, metronidazole, and acyclovir over an eight week period showed remarkable improvements in joint involvement, associated symptoms, energy level, and function, following treatment. More particularly, the study results showed that following treatment with an exemplary combination in accordance with the invention, the overall number of affected joints plus areas demonstrating symptomatology (e.g., large joints, spinal area, Achilles insertion, and hands) decreased by over 80%. Overall symptoms in affected joints and areas improved by greater than 87%. Seven of the eleven patients reported a 100% improvement in energy level, while the remaining patients reported improvements in energy level ranging from 60% to 90%. Finally, at the end of treatment, the majority of patients reported marked improvement in their ability to perform physical activities such as traversing stairs and walking.

Thus, as can be seen, the combination of the invention provides a notable and surprisingly effective treatment for reactive arthritis as well as osteoarthritis and other related arthritic and inflammatory conditions such as bursitis.

II. E. Additional Active Agents

In addition to the above-described combination of drug types, a therapeutic composition of the invention may optionally include one or more additional active agents, herbs, vitamins, minerals, or other supplements. If desired, in addition to the "core" components, i.e., at least two of, and preferably each of (i) an antiviral, (ii) a broad-spectrum antibiotic, and (iii) an anti-protozoal, a composition of the invention may, but does not necessarily, also include more than one antiviral compound, and/or more than one broad-spectrum antibiotic, and/or more than one anti-protozoal compound.

Representative additional components of an anti-reactive arthritis/osteoarthritis therapeutic composition of the invention include amino acids such as L-lysine, isonicotinic acid hydrazide (InH, isoniazide), pyridoxine hydrochloride, glucosamine, chondroitin, methylsulfonylmethane (also known as methyl sulfone), S-adenosylmethionine, minerals such as manganese, magnesium, and zinc, vitamins such as niacinamide, vitamin C, vitamin D, and vitamin E, bromelain, Echinacea, Evening of Primrose oil, fish oil, folic acid, garlic, ginger, ginko, ginseng, kava kava, St. John's wort, boswellia, valerian, desalinated seawater, supplemental blends such as those available from Essence of Life, LLC, and the like.

II. F. Excipients/Additives

Optionally, the compositions of the invention may further comprise one or more pharmaceutically acceptable excipients to provide a pharmaceutical composition. Exemplary excipients include, without limitation, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

A composition of the invention may include one or more carbohydrates such as a sugar, a derivatized sugar such as an alditol, aldonic acid, an esterified sugar, and/or a sugar polymer. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Also suitable for use in the compositions of the invention are potato and corn-based starches such as sodium starch glycolate and directly compressible modified starch.

Further representative excipients include inorganic salt or buffers such as citric acid, sodium chloride, potassium chloride, sodium sulfate, potassium nitrate, sodium phosphate monobasic, sodium phosphate dibasic, and combinations thereof.

The composition may also include an antimicrobial agent, e.g., for preventing or deterring microbial growth. Non-limiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

A composition of the invention may also contain one or more antioxidants. Antioxidants are used to prevent oxidation, thereby preventing the deterioration of the drug(s) or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition of the invention may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient, with concentrations less than 30% by weight most preferred.

These foregoing pharmaceutical excipients along with other excipients are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

III. Delivery Forms

The compositions encompass all types of formulations and in particular those that are suited for oral administration, e.g., tablets, lozenges, capsules, syrups, oral suspensions, emulsions, granules, and pellets. Alternative formulations include aerosols, transdermal patches, gels, creams, ointments, suppositories, powders or lyophilates that can be reconstituted, as well as liquids, such as for use in an oral or parenteral product.

Examples of suitable diluents for reconstituting solid compositions, e.g., prior to injection, include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned.

In turning now to oral delivery formulations, tablets can be made by compression or molding, optionally with one or more accessory ingredients or additives. Compressed tablets are prepared, for example, by compressing in a suitable tabletting machine, the active ingredients in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) and/or surface-active or dispersing agent.

Molded tablets are made, for example, by molding in a suitable tabletting machine, a mixture of powdered compounds moistened with an inert liquid diluent. The tablets may optionally be coated or scored, and may be formulated so as to provide slow or controlled release of the active ingredients, using, for example, hydroxypropylmethyl cellulose in varying proportions to provide the desired release profile. Tablets may optionally be provided with a coating, such as a thin film, sugar coating, or an enteric coating to provide release in parts of the gut other than the stomach. Processes, equipment, and toll manufacturers for tablet and capsule making are well-known in the art.

Capsule formulations may utilize either hard or soft capsules, including gelatin capsules or vegetarian capsules such as those made out of hydroxymethylpropylcellulose (HMPC). One preferred type of capsule is a gelatin capsule. Capsules may be filled using a capsule filling machine such as those available from commercial suppliers such as Miranda International or employing capsule manufacturing techniques well-known in the industry, as described in detail in *Pharmaceutical Capules,* 2$^{nd}$ Ed., F. Podczeck and B. Jones, 2004. Alternatively, capsule formulations may be prepared using a toll manufacturing center such as the Chao Center for Industrial Pharmacy & Contract Manufacturing, located at Purdue Research Park.

Formulations for topical administration in the mouth include lozenges comprising the active ingredients, generally in a flavored base such as sucrose and acacia or tragacanth and pastilles comprising the active ingredients in an inert base such as gelatin and glycerin or sucrose and acacia.

A pharmaceutical composition for topical administration may also be formulated as an ointment, cream, suspension, lotion, powder, solution, paste, gel, spray, aerosol or oil. Alternatively, the formulation may be in the form of a patch (e.g., a transdermal patch) or a dressing such as a bandage or adhesive plaster impregnated with active ingredients and optionally one or more excipients or diluents. Topical formulations may additionally include a compound that enhances absorption or penetration of the ingredients through the skin or other affected areas, such as dimethylsulfoxidem bisabolol, oleic acid, isopropyl myristate, and D-limonene, to name a few.

For emulsions, the oily phase is constituted from known ingredients in a known manner. While this phase may comprise merely an emulsifier (otherwise known as an emulgent), it desirably comprises a mixture of at least one emulsifier with a fat and/or an oil. Preferably, a hydrophilic emulsifier is included together with a lipophilic emulsifier that acts as a stabilizer. Together, the emulsifier(s) with or without stabilizer(s) make up the so-called emulsifying wax, and the wax together with the oil and/or fat make up the so-called emulsifying ointment base which forms the oily dispersed phase of cream formulations. Illustrative emulgents and emulsion stabilizers include Tween 60, Span 80, cetostearyl alcohol, myristyl alcohol, glyceryl monostearate and sodium lauryl sulfate.

Formulations for rectal administration are typically in the form of a suppository with a suitable base comprising, for example, cocoa butter or a salicylate.

Formulations suitable for vaginal administration generally take the form of a suppository, tampon, cream, gel, paste, foam or spray.

Formulations suitable for nasal administration, wherein the carrier is a solid, include a coarse powder having a particle size, for example, in the range of about 20 to about 500 microns. Such a formulation is typically administered by rapid inhalation through the nasal passage, e.g., from a container of the powder held in proximity to the nose. Alternatively, a formulation for nasal delivery may be in the form of a liquid, e.g., a nasal spray or nasal drops.

Aerosolizable formulations for inhalation may be in dry powder form (e.g., suitable for administration by a dry powder inhaler), or, alternatively, may be in liquid form, e.g., for use in a nebulizer. Nebulizers for delivering an aerosolized solution include the AERx™ (Aradigm), the Ultravent® (Mallinkrodt), and the Acorn II® (Marquest Medical Products). A composition of the invention may also be delivered using a pressurized, metered dose inhaler (MDI), e.g., the Ventolin® metered dose inhaler, containing a solution or suspension of a combination of drugs as described herein in a pharmaceutically inert liquid propellant, e.g., a chlorofluorocarbon or fluorocarbon.

Formulations suitable for parenteral administration include aqueous and non-aqueous isotonic sterile solutions suitable for injection, as well as aqueous and non-aqueous sterile suspensions.

Parenteral formulations of the invention are optionally contained in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the types previously described.

A formulation of the invention may also be a sustained release formulation, such that each of the drug components is released or absorbed slowly over time, when compared to a non-sustained release formulation. Sustained release formulations may employ pro-drug forms of the active agent, delayed-release drug delivery systems such as liposomes or polymer matrices, hydrogels, or covalent attachment of a polymer such as polyethylene glycol to the active agent.

In addition to the ingredients particularly mentioned above, the formulations of the invention may optionally include other agents conventional in the pharmaceutical arts and particular type of formulation being employed, for example, for oral administration forms, the composition for oral adminsitration may also include additional agents as sweeteners, thickeners or flavoring agents.

The compositions of the present invention may also be prepared in a form suitable for veterinary applications.

Preferably, the anti-arthritic compositions described herein are in unit dosage form, meaning a quantity of a combination of drugs of the invention, appropriate for a single dose, or multiple doses, in one or more premeasured or pre-packaged forms. One particularly preferred type of solid dosage form is a capsule containing each of an antiviral compound, a broad-spectrum antibiotic, and an antiprotozoal compound, or any two of the foregoing. Dosage forms and modes of administration are discussed in greater detail in the sections that follow.

IV. Method of Diagnosis

Broadly speaking, reactive arthritis is usually defined as a sterile joint inflammation triggered by a distant infection, with no cultivable microbes in the joints (Toivanen, A., Toivanen, P., *Best Practice & Research Clinical Rheumatology*, Vol 18, No. 5p 689-703 (2004)), oftentimes making diagnosis difficult. A number of microbes can trigger the disease such as *Campylobacter, Chamydia, Clostridium, Salmonella, Shigella, Yersinia, Borrelia, Brucella, Haemophilus, Hafnia, Leptospira, Mycobacterium, Neisseria, Staphylococcus, Streptococcus, Ureaplasma* and *Vibrio*. Although viable microbes have not been detected, traces of bacterial components have been detected at sites of inflammation. Moreover, the elimination of the triggering infection, for example, by antibiotic treatment, does not prevent the development of reactive arthritis once the pathogenic process has started (Toivanen, A., *Drugs* 2001; 61:343-351.).

Typically, after contracting the triggering infection, some time elapses before the clinical signs of the primary disease appear. One possible predisposing factor for reactive arthritis is the HLA-B27 antigen. However, not all B-27 positive individuals develop reactive arthritis even if they contract a triggering infection, while some B27-negative individuals do. However, there are no definite blood markers used for the diagnosis of the disease.

Clinical features of reactive arthritis often include acute synovitis, typically at a lower limb, knee effusions, fusiform dactylitis (sausage digits), enthesitis (inflammation at ligament or tendon attachments to bone)—most often observed as Achilles tendonitis or plantar fasciitis, and thoracic and lumbar spine pain. Most commonly, the large joints of the lower extremities are affected, although any joint, including the wrists and small joints of the hand, may be inflamed. Although less frequent, patients may also exhibit mucocutaneous lesions or conjunctivitis. The most commonly observed dermal affliction is the psoriasis-like *pustuosis palmoplantaris* or *keratoderma blenorrhagicum*. The patients may also eventually exhibit the signs and symptoms of osteoarthritis, such as joint stiffness, tenderness, pain, fatigue, and radiologic features (e.g., osteophytes).

Additional laboratory and radiologic investigations may also aid in a diagnosis of reactive arthritis. The erythrocyte sedimentation rate (ESR) and C-reactive protein (CRP) values in patients suffering from classic reactive arthritis may be elevated, however, the sedimentation rate is quite often within normal range. In the acute phase of ReA, leukocytosis also may be observed. Radiologic examinations may reveal soft tissue swelling, juxta-articular osteoporosis, periosteal reaction and proliferation at tendon insertion sites. Occasionally, plantar spurs may be seen. As stated previously, in reactive arthritis, bacteria are not demonstrable either by staining or culture.

Additionally, the clinician may attempt to isolate triggering microbes from various sites if possible including the throat, urogenital tract or feces, using for example, PCR, for detection. Further, antibodies against known causative agents such as *Yersinia, Salmonella, Campylobacter, Chlamydia, Neisseria gonorrhoeae, Borrelia burgdorferi*, may be detectable. For instance, in ReA, IgA type antibodies may be elevated and can be detected, e.g., by enzyme immunoassays. Most typically, however, the offending organism cannot be isolated or identified.

In patients suffering from osteoarthritis, laboratory studies are most often within normal range including sedimentation rate and leucocyte count. Radiographic studies, however, often reveal characteristic changes indicative of osteoarthritis including non-uniform joint space loss, osteophyte formation, cyst formation and subchondral sclerosis (Swagerty, D. L., et al., *American Family Physician*, Vol. 64, No. 2, 2001, 279-86). In early stage osteoarthritic patients, initial radiographs may not show all of the above indicators. At first, only minimal, non-uniform joint space narrowing may be present, and the involved joint spaces may simply have an asymmetric distribution. To date, osteoarthritis has not been typically related to an on-going infectious process.

V. Method of Administration

As set forth above, methods of delivery include but are not limited to, oral, intra-arterial, intramuscular, intravenous, intranasal, and inhalation routes. A preferred delivery route is oral. Suitable modes of delivery will be apparent based upon the particular combination of drugs employed and their known administration forms.

More particularly, a combination anti-reactive arthritis/osteoarthritis composition of the present invention may be administered for therapy by any suitable route, including without limitation, oral, rectal, nasal, topical (including transdermal, aerosol, buccal and sublingual), vaginal, penile, parenteral (including subcutaneous, intramuscular, intravenous and intradermal) and pulmonary. The preferred route will, of course, vary with the condition and age of the recipient, the particular disease state being treated, and the specific combination of drugs employed.

The combination of the invention may be administered as a single combination composition comprising at least two of, and preferably each of: (i) an antiviral compound, (ii) a broad-spectrum antibiotic, and (iii) an anti-protozoal compound, in unit dosage form. In terms of patient compliance and ease of administration, such an approach is preferred, since patients are often adverse to taking multiple pills or capsule, often multiple times daily, over the duration of treatment. Alternatively, albeit less preferably, the combination of the invention is administered as separate dosage forms, or even as one combination form comprising two of the active agent classes, in addition to one of the actives being administered separately. Relating to the latter, for instance, one single combination composition may comprise an antiviral and a broad-spectrum antibiotic, which is then administered separately from the anti-protozoal compound. Alternatively, a single combination composition comprising an antiviral and an anti-protozoal is administered separately from the broad-spectrum antibiotic. In yet another alternative, a single combination composition comprising a broad-spectrum antibiotic and an anti-protozoal is administered separately from the antiviral. In instances in which the drugs comprising the therapeutic composition of the invention are administered as separate dosage forms and co-administration is required, each of the different active agents may be administered simultaneously, sequentially in any order, or separately.

VI. Kits

Also provided herein is a kit or package containing at least one combination composition of the invention, accompanied by instructions for use.

For example, in instances in which each of the drugs themselves are administered as individual or separate dosage forms (e.g., capsules or tablets), the kit comprises each of the drugs making up the composition of the invention, along with instructions for use. The drug components may be packaged in any manner suitable for administration, so long as the packaging, when considered along with the instructions for administration, clearly indicates the manner in which each of the drug components is to be administered. Alternatively, each of the drug components of the combination may be combined into a single administrable dosage form such as a capsule.

For example, for an illustrative kit comprising an antiviral compound (AV), a broad-spectrum antibiotic (BSA) and an antiprotozoal compound (AP), the kit may be organized by any appropriate time period, such as by day. As an example, for Day 1, a representative kit may comprise unit dosages of each of the AV, BSA, and AP. If each of the drugs is to be administered twice daily, then the kit may contain, corresponding to Day 1, two rows of unit dosage forms of each of the AV, BSA, and AP, for example, in capsule form, with instructions for the timing of administration. Alternatively, if one or more of the drugs differs in the timing or quantity of drug to be administered in comparison to the other drug members of the combination, then such would be reflected in the packaging and instructions. For example, if the AV and BSA are to be administered twice daily, and the AP is to be taken only once daily, exemplary Day 1 packaging might correspond to unit dosage forms of each of the AV, BSA, and AP as "Day 1, Dose 1", along with dosage forms for only the AV and BSA corresponding to "Day 1, Dose 2".

According to a preferred embodiment, the kit includes each of minocycline hydrochloride, metronidazole, and acyclovir, either contained in a single capsule, or in individual unit dosage forms accompanied by instructions for use.

Various embodiments according to the above may be readily envisioned, and would of course depend upon the particular combination of drugs employed for treatment, their corresponding dosage forms, recommended dosages, intended patient population, and the like. The packaging may be in any form commonly employed for the packaging of pharmaceuticals, such as medication punch cards or blisters, and may utilize any of a number of features such as different colors, wrapping, tamper-resistant packaging, blister paks, dessicants, and the like.

VII. Dosages

Therapeutic amounts can be empirically determined and will vary with the particular condition being treated, the subject, and the efficacy and toxicity of each of the active agents contained in the composition. The actual dose to be administered will vary depending upon the age, weight, and general condition of the subject as well as the severity of the condition being treated, the judgment of the health care professional, and particular combination being administered.

Therapeutically effective amounts can be determined by those skilled in the art, and will be adjusted to the requirements of each particular case. Generally, a therapeutically effective amount will range from about 25 mg to about 4 grams of each active agent (AV, BSA or AP), preferably in doses such as the following. Alternatively, a therapeutically effective amount may range from about 50 mg to about 2 grams of each active agent (AV, BSA or AP), or from about 75 mg to about 1 gram of each active agent, or from about 100 mg to about 1 gram of active agent, or from about 200 mg to about 1 gram of each active agent. Unit dosage forms of each active agent are typically selected from the following: 10 mg, 25 mg, 50 mg, 100 mg, 200 mg, 250 mg, 300 mg, 400 mg, 500 mg, 600 mg, 700 mg, and 750 mg.

Representative dosages of each active agent are typically selected from the group consisting of: from about 25-1000 mg/twice daily, from about 50 to about 750 mg/twice daily, from about 100 to about 700 mg twice daily, from about 250-700 mg twice daily, from about 200 to about 600 mg twice daily, from about 25-1000 mg/thrice daily, from about 50 to about 750 mg/thrice daily, from about 100 to about 700 mg thrice daily, from about 250-700 mg thrice daily, from about 200 to about 600 mg thrice daily, from about 25-1000 mg/four times daily, from about 50 to about 750 mg/four times daily, from about 100 to about 700 mg four times daily, from about 250-700 mg four times daily, and from about 200 to about 600 mg four times daily.

Illustrative doses of particular active agents include the following. For example, for compositions or methods employing the antiviral compound, acyclovir, the daily dose will typically range from about 100 mg to about 4 grams, or from about 200 mg to about 3 grams, with a preferred dose of about 50-400 mg twice daily. That is to say, a preferred dose of acyclovir is typically 50 mg, or 100 mg, or 200 mg, or 300 mg or 400 mg twice daily. Similarly, the total daily dose of the valine ester form of acyclovir, valcyclovir, will typically range from about 125 mg to about 4 grams daily, with a preferred dose of 50-500 mg twice daily. Preferred dosages of valcyclovir are 50 mg or 100 mg or 200 mg or 300 mg or 400 mg or 500 mg, twice daily.

For compositions employing the broad-spectrum antibiotic, minocycline, a typical daily dose ranges from about 50 mg to about 500 mg. Preferably, a drug such as minocycline is administered at an initial dose of 25 mg to 200 mg (e.g., 25 mg or 50 mg or 100 mg or 150 mg or 250 mg), followed by a dose of 25, 50, 100, or 250 mg once or twice daily. Most preferred is administration of 25, 50, 100, or 250 mg twice daily. In turning now to another representative broad-spectrum antibiotic, amoxicillin, a preferred daily dose is from 25-500 mg twice per day, with a total daily dose of from about 50 mg to 3 gm. The broad-spectrum antibiotic, azithromycin, is typically administered at doses ranging from about 25 mg to 500 mg, or from 50 mg to 125 mg twice per day. The overall daily dose of azithromycin will generally range from about 50 mg to about 2 gm. The broad spectrum antibiotic, telithromycin, is typically administered at a dosage of about 25 mg to 400 mg twice per day, with overally daily dosages ranging from about 50 mg to 2 gm.

Turning now to the anti-protozoal compound, metronidazole, illustrative dosages range from about 100 mg to 1,000 mg daily, with a preferred dosing schedule of about 50 to 500 mg administered twice daily. Representative dosages include 50, 75, 125, 150, 175, 200 or 250 mg twice daily.

Practically speaking, a unit dose of any given composition of the invention or active agent can be administered in a variety of dosing schedules, depending on the judgement of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth.

Commencement of treatment can begin at any time, and does not necessarily begin during the stage of intial infection. In fact, commencement of therapy can, and, in most instances, does take place after an initial infection has passed and viable microbes are no not detectable in the subject. The duration of treatment will depend of course on the severity of the condition, the age and condition of the patient, and the like, and will be readily determined by one of skill in the art. Illustrative courses of therapy include 1 week, 2 weeks, 3, weeks, 4 weeks, 5 weeks, 6 weeks, 7 weeks, 8 weeks, 9 weeks, 10 weeks, 11 weeks, 12 weeks, 3.5 months, 4 months, 4.5 months, 5 months, 6 months, or longer as needed. Treatment is generally continued until resolution of all symptoms is effected or until the patient reports (or the physician notes) either no further improvement, or only minor or insignificant improvement in the subject's remaining symptoms with continued anti-reactive arthritis/osteoarthritis therapy as described herein.

It is to be understood that while the invention has been described in conjunction with preferred specific embodiments, the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

EXAMPLES

Example 1

In-Vivo Study

Treatment of Human Subject Diagnosed with Reactive Arthritis with Combination of Metronidazole, Valacyclovir, and Minocycline A 77-year old female patient presented with complaints of neck, upper back, lower back, bilateral shoulder, bilateral wrist, digits of hands, bilateral hip, and bilateral ankle pains that had lasted for years. The patient complained of associated stiffness in those same joints. The patient was examined by touching the affected joints and looking for signs of swelling and inflammation, and noting her response to questions regarding degree of pain, tenderness, and stiffness. Tenderness was evaluated by the practicing physician as 'slight' to 'severe', with a majority of the joints falling within the 'moderate' category.

Her physical examination was remarkable for tenderness at her neck, right shoulder, elbow bilaterally, wrist bilaterally, the metacarpal phalangeal and the proximal interphalangeal joints of her right hand, hip bilaterally, knee bilaterally, and the Achilles insertion area bilaterally. The patient reported that the initial degree of pain throughout the body as 5-8 on a unilinear pain scale of 1-10 (1=no pain, 10=severe pain).

Blood was drawn from the patient and sedimentation rate (sed rate) and rheumatoid factor (RF) tests were conducted. The sed test measures how quickly red blood cells settle in a test tube in one hour. If present, certain proteins cause red blood cells to stick together and fall more quickly than normal to the bottom of the tube. The more red cells that fall to the bottom of the test tube in one hour, the higher the sed rate. A rheumatoid factor test measures the amount of the RF antibody present in most people with rheumatoid arthritis. The results from both tests were normal.

Based upon the above, this patient was diagnosed with reactive arthritis. She was started on a treatment of single capsules, each capsule containing—125 mg of metronidazole, 250 mg of valacyclovir hydrochloride, and 50 mg of minocycline hydrochloride, taken orally twice daily.

After 69 days of such treatment, in a follow-up examination, the patient reported pain in the palm of her left hand only, and no more stiffness. A physical examination failed to reveal any remaining tenderness.

For this patient, the course of treatment resulted in a near complete resolution of pain (with the exception of the left palm), stiffness, and tenderness.

Example 2

In-Vivo Study

Treatment of Human Subject Diagnosed with Reactive Arthritis with Combination of Acyclovir and Minocycline A 52 year-old male presented with complaints of bilateral knee and left wrist pain. He also reported associated morning stiffness.

The patient was diagnosed with reactive arthritis. He was started on a course of treatment with minocyline hydrochloride 100 mg BID (twice daily) and acyclovir 400 mg BID. The treatment resulted in significant improvement, but not total resolution of his complaints of pain and stiffness in his knees and left wrist.

Example 3

In-Vivo Study

Treatment of Human Subject Diagnosed with Reactive Arthritis with Combination of Metronidazole and Minocycline A 45 year-old male presented with multiple joint pains and associated stiffness.

The patient was diagnosed with reactive arthritis, and placed on a treatment regime of metronidazole (250 mg, twice daily) and minocycline (100 mg, twice daily).

In a follow-up examination, the patient reported a reduction in pain severity and a slight decrease in stiffness in the affected joints.

Example 4

In-Vivo Study

Short Term Treatment of Human Subject Diagnosed with Reactive Arthritis with Metronidazole and Minocycline Accompanied by Concurrent Long Term Treatment with L-Lysine and InH An adult male presented with symptoms involving his knees, ankles, elbows, wrist and carpophalengeal joints as follows. The patient reported that stooping activities caused severe pain in his knees. Simple driving activities caused pain in his elbows, wrists, and knees. He was unable to run or jog because of pain in his knees and ankles. Lifting objects weighing more than five pounds resulted in wrist and hand pain.

The patient was treated with metronidazole (250 mg BID) and minocycline hydrochloride (100 mg BID) for thirty days and simultaneously with L-lysine (1 g QD) and InH (300 mg QD) for one year. Positive symptomatic relief was achieved within two weeks of treatment by administration of the combination of metronidazole, minocycline hydrochloride, InH, and L-lysine. Complete recovery was reported at the end of the course of treatment with InH. The patient has continued taking L-lysine due to the possible idiologic role of herpes simplex, and its tendency to remain present in a dormant state.

The patient now has no problems lifting, running or driving. However, it should be kept in mind that infections can reoccur and follow-up treatment with at least minocycline hydrochloride and metronidazole may be necessary again in the future, depending upon the potential reoccurrence of joint pain.

Example 5

In-Vivo Study

Short Term Treatment of Human Subject Diagnosed With Reactive Arthritis with Metronidazole and Minocycline Accompanied by Concurrent Long Term Treatment with L-Lysine and InH A seventy-one year old female was diagnosed as suffering from reactive arthritis. Her symptoms included joint pain and stiffness involving her knees, wrists, elbows, and hips. Pain in multiple joints caused difficulty in (i) walking, (ii) rising from a sitting position to a standing position, and (iii) sitting down from a standing position. The patient was unable to run or jog. The patient was treated with a short course of metronidazole (250 mg BID) and minocycline hydrochloride (100 mg BID) for thirty days. The patient was treated concurrently, and over a longer term (one year) with L-lysine (1 g QD) and InH (300 mg QD).

Treatment resulted in resolution of all joint pain. Following treatment, the patient was able to walk without pain, rise from a sitting position, and sit down from a standing position without difficulty. The patient was also able to jog without discomfort or difficulty. No adverse side effects were reported during the course of treatment, and no adverse effects have been observed or reported as a result of treatment. In the above cases, the treatment has resulted in a dramatic elimination of symptoms of the associated disease state.

Example 6

In-Vivo Study

Treatment of Human Subject Diagnosed with Reactive Arthritis with a Combination of L-Lysine, Minocycline, Metronidazole, and Valacyclovir A 46-year-old male initially presented with severe symptoms of reactive arthritis, including joint swelling and joint contractures. His symptoms had been previously diagnosed as psoriatic arthritis.

The patient's joint symptoms included long-term pain and stiffness of multiple joints. Such pain had been ongoing for at least five years. The subject possessed sausage-shaped digits on his hands and experienced early flexion contractures at the PIP (proximal-interphalangeal) joint of such digits bilaterally. When this patient was initially examined, he had difficulty twisting lids on containers with his hands, grasping small objects, and experienced extreme discomfort with prolonged reaching above his head. The patient was also unable to run, jog, or jump.

The patient was treated with a combination of L-lysine (1 g QD), minocycline hydrochloride (100 mg BID), metronidazole (250 mg BID), and valacyclovir hydrochloride (500 mg BID). Within 48 hours of commencing treatment, the patient experienced a significant decrease in pain and stiffness. Within one week of treatment, the joint deformities of the digits of his hands had resolved. After two weeks of treatment, the patient was able to run, jog, and jump. His grasping abilities significantly improved, and after one month he was able to return to work as a machinist.

Example 7

In-Vivo Study

Treatment of Human Subject Diagnosed with Reactive Arthritis with a Combination of L-Lysine Minocycline and Metronidazole A 75-year-old female previously diagnosed as having osteoarthritis was re-diagnosed as suffering from reactive arthritis, based upon clinical evidence of an enthesopathy of the Achilles insertion—a characteristic of reactive arthritis. The patient complained of pain and stiffness in joints of the shoulders, elbows, Achilles insertion, and hands. The patient also experienced extreme difficulty in standing from a seated position, and walking with a prescribed assistive device (4-leg walker).

Initial treatment consisted of L-lysine (1 g QD), minocycline hydrochloride (100 mg BID), and metronidazole (250 mg BID), administered separately over a course of 138 days. The patient continued this dosing regimen for several months with minimal and transient improvement in arthritic symptoms. At this point, the practicing physician added valacyclovir hydrochloride (500 mg BID) to the initial treatment regimen of L-lysine, minocycline hydrochloride, and metronidazole, administered separately, over a time course of an additional 351 days.

Within 48 hours of dosing with the modified treatment, the patient reported a significant reduction in pain and stiffness. Within one month, the patient reported resolution of all joint pain, with the exception of occasional intermittent pain in the lower back region, and was able to ambulate without the use of a walker.

Example 8

In-Vivo Study

Treatment of Human Subject Diagnosed with Reactive Arthritis with a Combination of L-Lysine, Minocycline Metronidazole and Valacyclovir A 28-year-old male diagnosed with reactive arthritis presented with complaints of multiple joint pain and stiffness. His symptoms caused him difficulty in raising his arms above his head, driving and bending over.

Treatment was commenced with a combination of L-lysine (1 g QD), minocycline hydrochloride (100 mg BID), metronidazole (250 mg BID), and valacyclovir hydrochloride (500 mg BID). Within 48 to 72 hours, the patient experienced a significant diminution in his joint pain severity and joint stiffness. After one month of treatment, his joint pains had resolved, with the exception of occasional slight pain at one shoulder. The patient's complaints regarding his inability to comfortably raise his arms above his head, driving and bending over have resolved.

Example 9

In-Vivo Study

Treatment of Human Subject Diagnosed with Reactive Arthritis with a Combination of L-Lysine Minocycline, Metronidazole and Acyclovir A 56-year-old male, previously diagnosed with osteoarthritis, presented with complaints of pain in his spine, shoulders, elbows, wrists, fingers, hips, knees, ankles, and heels. The patient also reported associated morning stiffness and complained of difficulty in walking, climbing stairs, and jogging. After examination, the patient was re-diagnosed with reactive arthritis, and placed on a combination treatment regime of acyclovir, L-lysine, metronidazole, and minocycline.

The treatment resulted in a dramatic diminution of the patient's pain within two weeks after commencing treatment. After two weeks of treatment, the patient's difficulties with walking and climbing stairs were also resolved.

Example 10

In-Vivo Study

Treatment of Human Subject Diagnosed with Reactive Arthritis with a Combination of L-Lysine, Minocycline Metronidazole and Acyclovir A 78-year-old male, previously diagnosed with osteoarthritis, presented with complaints of pain in his cervical spine, lumbar spine and knees. The patient complained of associated morning stiffness in those areas, as well as difficulty in standing—which particularly aggravated his lower back pain. The patient was diagnosed with reactive arthritis, and placed on combination therapy with acyclovir (400 mg BID), L-lysine (1 g QD), metronidazole (250 mg BID), and minocycline hydrochloride (100 mg BID).

The treatment effected resolution of the patient's neck and lower back pain and his knee pain within sixty days.

Example 11

In-Vivo Study

Treatment of Human Subject Diagnosed with Reactive Arthritis with a Combination of L-Lysine, Minocycline, Metronidazole and Acyclovir A 50-year-old male whose status was post right hip replacement, secondary to avascular necrosis, presented with complaints of multiple joint pain. Evaluation determined that the patient was suffering from reactive arthritis. The patient had been previously treated with nonsteroidal antiinflammatory drugs (NSAIDs). Based upon the diagnosis, the patient was started on a course of treatment of acyclovir (400 mg BID), L-lysine (1 g QD), metronidazole (250 mg BID), and minocycline (100 mg BID), administered separataely.

Within three weeks of treatment initiation, the patient reported a significant improvement in arthritic symptoms. Treatment duration was 330 days.

Example 12

In-Vivo Study

Treatment of Human Subject Diagnosed with Reactive Arthritis with a Combination of L-Lysine, Minocycline, Metronidazole, Acyclovir InH, and Pyridoxine A 31-year-old male presented with complaints of shoulder, hand, knee, and foot pain. Swelling in the patient's hands was also noted. The patient was unable to even jog without knee pain. The patient also exhibited a positive skin test for TB. Based upon a diagnosis of reactive arthtitis, the patient was placed on a treatment regime of a combination of InH (300 mg QD), metronidazole (250 mg BID), minocycline (100 mg BID), acyclovir (400 mg BID), L-lysine (1 g QD), and pyridoxine (50 QD).

Within three months after commencing treatment, the patient reported total resolution of all symptoms. The patient currently runs on a daily basis without pain and actively works out in the weight room without pain. Additionally, the patient has not experienced any interim swelling of his hands.

Example 13

Treatment of 11 Human Subjects Diagnosed with Non-Nodal Osteoarthritis with a Combination Therapy of Minocycline, Metronidazole, and Acyclovir ("Triple Combination")

Eleven patients were selected for an eight week course treatment of minocycline HCl, metronidazole and acyclovir ("triple combination"), dosed orally, twice daily.

Inclusion in Study: For inclusion in the study, patients must have minimally exhibited one of the classifications from Table 3. Ten patients met criteria for osteoarthritis of the knee, and one patient met the criteria for osteoarthritis of the hip.

TABLE 3

CRITERIA FOR CLASSIFICATION OF IDIOPATHIC OSTEOARTHRITIS (OA) OF THE KNEE

| Clinical | Clinical & Radiographic | Clinical & Laboratory |
|---|---|---|
| Knee pain + | Knee pain + | Knee pain + |
| at least 3 of 6: | Osteophytes + | at least 5 of 9: |
| Age >50 years | at least 1 of 3: | Age >50 years |
| Stiffness <30 minutes | Age >50 years | Stiffness <30 minutes |
| Crepitus | Stiffness <30 minutes | Crepitus |
| Bony tenderness | Crepitus | Bony tenderness |
| Bony enlargement | | Bony enlargement |
| No palpable warmth | | No palpable warmth |
| | | ESR <40 mm/hour |
| | | RF <1:40 |
| | | Synovial fluid signs of OA |

Prior to treatment initiation, all eleven patients presented with complaints of multiple joint pains ranging from one to thirty years in duration, and were between ages 46 to 81. Pre-treatment laboratory results (SED rate, rheumatoid factor, AST (SGOT), alkaline phosphate, total biliruben, total protein, albumin, BUN, and creatinine) were collected for each patient. Each patient exhibited laboratory results within normal limits; antinuclear antibody results were all negative.

Patients were allowed to use pain relief medications (NSAID's, COX-2 inhibitors, acetaminophen, narcotic analgesics) throughout the study, but were instructed to report any frequency or dosage changes to pre-treatment pain relief medications throughout the course of the study.

In this regard, patient 001/EE voluntarily decreased dosage of Celebrex within eight days of treatment and discontinued use of Celebrex within 29 days of treatment. Patient 003/MB voluntarily discontinued the use of Vioxx within 21 days of treatment. Patient 006/DH decreased the dosage of tylenol with codeine within 12 days of treatment. Patient 007/RC discontinued the use of Vioxx within two months of treatment. Patient 010/AL decreased the dosage of Ultram within two months of treatment.

Triple Combination Therapy—Dosages. The triple combination medication administered was a single oral capsule containing minocycline hydrochloride 50 mg, metronidazole 125 mg, and acyclovir 200 mg. The recommended adult dosage was 2 capsules twice daily by mouth.

Patient 001/EE experienced episodes of dizziness within 8 days of treatment and voluntarily decreased the triple combination frequency from 2 capsules twice daily to 2 capsules once daily. These reported episodes of dizziness resolved, and on day 14, the triple combination frequency was increased to the recommended frequency of 2 capsules twice daily. Between days 14 and 22, the patient again reported experiencing episodes of dizziness and the patient returned to taking 2 capsules daily through the rest of the study. After day 22, the patient's dizziness resolved and did not reoccur. Patient 011/NM experienced episodes of dizziness and abdominal pain within 11 days of treatment and the patient voluntarily discontinued treatment on day 16.

Treatment Duration: The recommended treatment duration was approximately 8 weeks. Ten of the eleven patients received therapy no more than 56 days with one subject receiving treatment for 16 days.

Clinical Evaluations: Patients attended no less than two clinic evaluations at the beginning and end of treatment. Each clinic visit (to be conducted by the practicing physician) included the following:

Patient assessment of pain in large joints, spinal area, achilles insertion, and hands using a progressive numeric scale of 0-10 (0=no pain, 10=severe pain).

Patient assessment of stiffness in large joints, spinal area, achilles insertion, and hands using the average number of hours in a 24 hour day in which the patient experiences stiffness.

Patient assessment of fatigue based upon a total body assessment using a progressive numeric scale of 0-10 (0=no fatigue, 10=severe fatigue).

Patient assessment of physical function at the beginning and end of treatment.

Physician assessment of tenderness in large joints, spinal area, achilles insertion, right hand, and left hand using a progressive numeric scale of 0-3 (0=no tenderness, 1=slight tenderness, 2=moderate tenderness, 3=severe tenderness).

TABLE 4

DESCRIPTION OF JOINT CATEGORIES

| Large Joints | Spinal Area | Achilles Insertion | Hands | Right Hand [tenderness only] | Left Hand [tenderness only] |
|---|---|---|---|---|---|
| R shoulder | cervical spine | R achilles | R hand | carpal - metacarpal 1 | carpal - metacarpal 1 |
| L shoulder | | | | | |
| R elbow | thoracic spine | L achilles | L hand | | |
| L elbow | | | | metacarpal - phalangeal 1-5 | metacarpal - phalangeal 1-5 |
| R wrist | lumbosacral spine | | | | |
| L wrist | | | | | |
| R hip | | | | proximal - interphalangeal 1-5 | proximal - interphalangeal 1-5 |
| L hip | | | | | |
| R knee | | | | | |
| L knee | | | | | |
| R ankle | | | | | |
| L ankle | | | | | |

The efficacy data is presented subject-by-subject in a series of tables in which arthritic symptoms of pain, stiffness, tenderness, and fatigue are quantified according to defined scales of measurement pertaining to individual joints. Functionality associated with these joints and global values were calculated to assess overall symptom improvement within each subject and amongst all subjects.

Symptom Assessments: All assessments were made at baseline, interim (approximately one month), and at the end of treatment (approximately two months).

Arthritic pain was evaluated in the large joints of the body as follows: R/L shoulder, R/L elbow, R/L wrist, R/L hip, R/L knee, R/L ankle. Spinal pain was evaluated in the cervical, thoracic, and lumbosacral areas. The R/L achilles as well as the R/L hand were also assessed. A joint specific evaluation was additionally completed for tenderness of the large joints, spinal areas, achilles insertion, and R/L hand. Stiffness was evaluated for the large joints, spinal areas, achilles insertion, and R/L hand. A total body evaluation for fatigue (energy level) and physical function was also completed.

Pain (patient verbal assessment): Pain was assessed at three different intervals for each patient (baseline, interim, end of treatment) on a progressive numeric scale of 0-10 (0=no pain, 10=severe pain). From this data, an assessment was made of the overall decline of number of joints affected as well as the overall improvement of pain from baseline to interim, and baseline to end of treatment intervals.

Stiffness (patient verbal assessment): Stiffness was assessed at three different intervals for each patient (baseline, interim, end of treatment) as an average number of hours (based upon a 24 hour day) the patients experienced stiffness. From this data, an assessment was made of the overall decline of number of joints experiencing stiffness as well as the overall improvement of stiffness from baseline to interim, and baseline to end of treatment intervals.

Fatigue (patient verbal assessment): Fatigue was based upon a total body assessment at three different intervals for each patient (baseline, interim, end of treatment) on a progressive numeric scale of 0-10 (0=no fatigue, 10=severe fatigue). From this data, an assessment was made for the overall decline in fatigue as well as the overall improvement of energy level (table 7.4.4) from baseline to interim, and baseline to end of treatment intervals.

Function (patient verbal assessment): Physical Function was assessed at the beginning and end of treatment for each patient. Function was quantified on a numeric scale of 0-2 (0=inability to perform activity, 1=ability to perform activity with difficulty, 2=ability to perform activity without difficulty) in order to quantify patient's baseline physical impairments and end of treatment improvements.

Tenderness (physician assessment): Tenderness was assessed at three different intervals for each patient (baseline, interim, end of treatment) on a progressive numeric scale of 0-3 (0=no tenderness, 1=slight tenderness, 2=moderate tenderness, 3=severe tenderness). From this data, an assessment was made of the overall decline of number of joints affected as well as the overall improvement of tenderness from baseline to interim, and baseline to end of treatment intervals.

In summary, the data for pain, stiffness, and tenderness can be segregated between symptom resolution of joint involvement and overall symptom improvement, as shown below.

Results: Side effects were negligible, with only two patients exhibiting dizziness. One of these patients completed the recommended two month treatment course on a once/day reduced dosage; the other patient discontinued treatment on day 16.

Joint Involvement: The 'Joint Involvement Index' displays the results [decline %] from patient specific data which report the overall decline in the number of affected areas/joints from baseline to the end of treatment for symptoms of pain, stiffness, and tenderness. The index also shows a 'Subject Specific Global Result' (average of pain, stiffness, and tenderness across individual patients) and a 'Symptom Specific Global Result' (average of all study patients across individual symptoms).

At the end of treatment, the average number of large joints affected by symptoms of pain decreased by 89% (range of 75%-100%), stiffness by 84% (range of 50% to 100%), and tenderness by 80% (range of 40% to 100%), for an average decrease in the number of symptomatic large joints of 85% (range 61% to 100%).

The average number of spinal areas affected by symptoms of pain decreased by 89% (range 0% to 100%), stiffness by 78% (range 0% to 100%), and tenderness by 89% (range 33% to 100%), for an average decrease in the number of symptomatic spinal areas of 84% (range 0% to 100%).

The average number of achilles insertion areas affected by symptoms of pain decreased by 75% (range 0% to 100%), stiffness by 90% (range 50% to 100%), and tenderness by 86% (range 50% to 100%), for an average decrease in the number of symptomatic achilles insertion areas of 86% (range 50% to 100%).

The average number of hands affected by symptoms of pain decreased by 75% (range 0% to 100%), stiffness by 57% (range −100% to 100%; refer to footnote below joint involvement/hand stiffness table), tenderness of the right hand by 99% (range 91% to 100%), tenderness of the left hand by 88% (range 0% to 100%), for an average decrease in the number of symptomatic hands of 82% (range 33% to 100%).

These observations are also tabulated below:

Joint Involvement Decrease

TABLE 5

LARGE JOINTS

|  | Symptom | Average [%] | Range [%] |
|---|---|---|---|
| Large Joints: | Pain | 89 | 75-100 |
|  | Stiffness | 84 | 50-100 |
|  | Tenderness | 80 | 40-100 |
|  | Symptom Totals | 85 | 61-100 |

TABLE 6

SPINAL AREA

|  | Symptom | Average [%] | Range [%] |
|---|---|---|---|
| Spinal Area: | Pain | 89 | 0-100 |
|  | Stiffness | 78 | 0-100 |
|  | Tenderness | 89 | 33-100 |
|  | Symptom Totals | 84 | 0-100 |

TABLE 7

ACHILLES INSERTION

|  | Symptom | Average [%] | Range [%] |
|---|---|---|---|
| Achilles Insertion: | Pain | 75 | 0-100 |
|  | Stiffness | 90 | 50-100 |
|  | Tenderness | 86 | 50-100 |
|  | Symptom Totals | 86 | 50-100 |

TABLE 8

HANDS

|  | Symptom | Average [%] | Range [%] |
|---|---|---|---|
| Hands: | Pain | 75 | 0-100 |
|  | Stiffness | 57 | −100*-100 |
|  | Tenderness[R hand] | 99 | 91-100 |
|  | Tenderness[L hand] | 88 | 0-100 |
|  | Symptom Totals | 82 | 33-100 |

*One patient in the study demonstrated a negative response for stiffness. The average number of hands affected decreased by 57% when this patient is included in the data. The average no. of hands affected decreased by 67% when this patient is excluded from the data.

A comparison of the total number of symptomatic joints at baseline and at the end of treatment shows the marked effects of the triple combination therapy of minocycline hydrochloride, metronidazole, and acyclovir. The overall number of affected joints plus areas demonstrating symptomatology decreased by >80%. Tenderness in the small joints of the right hand showed the highest response with a decrease of 99% in the number of affected joints. Stiffness of the hands showed the least response, yet still remarkable, with a decrease of 57% in the number of affected joints.

Clinical evaluations may also include radiographic detection, CT imaging or magnetic resonance imaging (MRI). See, for example, Chan, W P., et al., *AJR Am J. Roentgenol.* 1991 October; 157(4): 799-806.

Symptom Improvement: The 'Symptom Improvement Index' displays the results [improvement %] from patient specific data which report the overall symptom improvement from baseline to the end of treatment for symptoms of pain, stiffness, and tenderness. The index also shows a 'Subject Specific Global Result' (average of pain, stiffness, and tenderness across individual patients) and a 'Symptom Specific Global Result' (average of all study patients across individual symptoms).

At the end of treatment, the large joint symptom improvement average for pain was 93% (range 79% to 100%), stiffness 82% (range −57% to 100%; refer to footnote below symptom improvement/large joint stiffness table), and tenderness 87% (range 55% to 100%), for an overall average symptom improvement for the large joints of 87% (range 33% to 100%).

The spinal area symptom improvement for pain was 96% (range 60% to 100%), stiffness 92% (range 50% to 100%), and tenderness 95% (range 67% to 100%), for an overall average symptom improvement for the spinal area of 94% (range 55% to 100%).

The achilles insertion symptom improvement for pain was 79% (range 30% to 100%), stiffness 100% (range 99% to 100%), and tenderness 91% (range 50% to 100%), for an overall average symptom improvement for the achilles insertion area of 92% (range 60% to 100%).

The hand symptom improvement for pain was 87% (range 56% to 100%), stiffness 95% (range −100% to 100%; refer to footnote below symptom improvement/hand stiffness table), tenderness of the right hand 100% (range 95% to 100%), tenderness of the left hand 92% (range 27% to 100%), for an overall average symptom improvement for the hands of 95% (range 82% to 100%). These observations are also tabulated below:

Symptom Improvement Summary

TABLE 9

LARGE JOINTS

|  | Symptom | Average [%] | Range [%] |
|---|---|---|---|
| Large Joints: | Pain | 93 | 79-100 |
|  | Stiffness | 82 | −57*-100 |
|  | Tenderness | 87 | 55-100 |
|  | Symptom Totals | 87 | 33-100 |

*One patient in the study demonstrated a negative response for stiffness. The average improvement of stiffness in the large joints improved by 82% when this patient is included in the data. The average improvement of stiffness in the large joints improved by 96% when this patient is excluded from the data.

TABLE 10

SPINAL AREA

|  | Symptom | Average [%] | Range [%] |
|---|---|---|---|
| Spinal Area: | Pain | 96 | 60-100 |
|  | Stiffness | 92 | 50-100 |
|  | Tenderness | 95 | 67-100 |
|  | Symptom Totals | 94 | 55-100 |

TABLE 11

ACHILLES INSERTION

| | Symptom | Average [%] | Range [%] |
|---|---|---|---|
| Achilles Insertion: | Pain | 79 | 30-100 |
| | Stiffness | 100 | 99-100 |
| | Tenderness | 91 | 50-100 |
| | Symptom Totals | 92 | 60-100 |

TABLE 12

HANDS

| | Symptom | Average [%] | Range [%] |
|---|---|---|---|
| Hands: | Pain | 87 | 56–100 |
| | Stiffness | 95 | −100*–100 |
| | Tenderness[R hand] | 100 | 95–100 |
| | Tenderness[L hand] | 92 | 27–100 |
| | Symptom Totals | 95 | 82–100 |

*One patient in the study demonstrated a negative response for stiffness. The average improvement of stiffness in the hands improved by 95% when this patient is included in the data. The average improvement of stiffness in the large joints improved by 100% when this patient is excluded from the data.

A comparison of symptom improvement at baseline and at the end of treatment also shows the outstanding affects of treatment. Overall symptoms in affected joints/areas improved by >87%. The small joints of the right hand showed the highest response with complete resolution (100% improvement) of tenderness. The achilles insertion area also showed complete resolution (100% improvement) of stiffness. Symptoms of pain within the achilles insertion area showed the least response, yet still remarkable, with an improvement of 79%.

Fatigue: Seven of the eleven patients reported 100% improvement in energy level (complete resolution of osteoarthritic fatigue) upon completion of treatment. The remaining patients showed improvements in energy level ranging from 60% to 90%.

Function: At the end of treatment, the majority of patients reported marked improvement in their ability to perform physical activities which had been previously limited due to arthritic symptoms. Pre-treatment data shows that the two most commonly reported activities proving to be difficult amongst the eleven patients were traversing stairs (6 of 11 patients) and walking (9 of 11 patients). Post-treatment data for these patients demonstrates a 100% improvement in their ability to traverse stairs and walk.

Considering all patients and variables measured, the triple combination therapy of minocycline hydrochloride/metronidazole/acyclovir remarkably improved symptoms of osteoarthritis (pain, tenderness, stiffness, fatigue) as well as improved physical function within all eleven patients evaluated. Additionally, the successful treatment of Patient 011/EE provided a surprising result—by demonstrating that the administration of lower than the standard dosage amounts of each of acyclovir, minocycline and metronidazole was as effective in improving the symptoms of osteoarthritis as the standard dose of each of the composition components. More specifically, Patient 011/EE was administered half the dosage amount administered to the other 10 patients in the study, but still demonstrated a notable improvement in the symptoms associated with osteoarthritis/reactive arthritis, as well as improved physical function.

What is claimed is:

1. A pharmaceutical composition effective in the treatment of an arthritic or inflammatory condition selected from reactive arthritis, osteoarthritis, and bursitis, comprising a combination of at least two of: (i) an antiviral compound, (ii) a broad-spectrum antibiotic, and (iii) an antiprotozoal compound.

2. The composition of claim 1, comprising an antiviral compound and a broad-spectrum antibiotic.

3. The composition of claim 1, comprising an antiviral compound and an antiprotozoal compound.

4. The composition of claim 1, comprising a broad-spectrum antibiotic and an antiprotozoal compound.

5. The composition of claim 1, wherein said composition comprises: (i) an antiviral compound, (ii) a broad-spectrum antibiotic, and (iii) an antiprotozoal compound.

6. The composition of claim 1, wherein said antiprotozoal compound is effective against anaerobic bacteria.

7. The composition of claim 1, wherein said antiprotozoal compound is selected from the group consisting of metronidizole, nitazoxanide, eflornithine, furazolidone, hydroxychloroquine, iodoquinol, and pentamidine.

8. The composition of claim 6, wherein said antiprotozoal compound is a nitroimidazole.

9. The composition of claim 8, wherein said antiprotozoal compound is metronidazole.

10. The composition of claim 1, wherein said antiviral compound is selected from the group consisting of nucleoside analogues, reverse transcriptase inhibitors, protease inhibitors, and entry inhibitors.

11. The composition of claim 1, wherein said antiviral compound is a nucleoside analogue.

12. The composition of claim 11, wherein said antiviral compound is acyclovir or valacyclovir.

13. The composition of claim 1, wherein said antiviral compound is acyclovir.

14. The composition of claim 1, wherein said broad specrum antibiotic is selected from the group consisting of aminoglycosides, macrolides, ketolides, quinolones, tetracyclines, and sulfonamides and beta-lactams.

15. The composition of claim 14, wherein said broad spectrum antibiotic is an aminoglycoside.

16. The composition of claim 14, wherein said broad spectrum antibiotic is a macrolide or a ketolide.

17. The composition of claim 14, wherein said broad spectrum antibiotic is a quinolone.

18. The composition of claim 14, wherein said broad spectrum antibiotic is a sulfonamide.

19. The composition of claim 14, wherein said broad spectrum antibiotic is a beta-lactam.

20. The composition of claim 14, wherein said broad spectrum antibiotic is a tetracycline.

21. The composition of claim 20, wherein said broad spectrum antibiotic is selected from the group consisting of tetracycline, doxycycline, meclocycline, minocycline, and oxytetracycline.

22. The composition of 1, comprising a nucleoside analogue, a tetracycline, and a nitroimidazole.

23. The composition of claim 1 further comprising a pharmaceutically acceptable excipient.

24. The composition of claim 5, further comprising a pharmaceutically acceptable excipient.

25. The composition of claim 1 or claim 5, comprising an admixture of said components.

26. The composition of claim 1 or claim 5, in a form suitable for oral or parenteral administration.

27. The composition of claim 26, in a form selected from the group consisting of tablet, capsule and oral suspension.

28. A kit comprising a combination of medicaments for the treatment of an inflammatory condition selected from reactive arthritis, osteoarthritis, and bursitis, comprising at least two of: (i) an antiviral compound, (ii) a broad-spectrum antibiotic, and (iii) an antiprotozoal compound, for simultaneous, sequential or separate use.

29. The kit of claim 28, wherein each of said medicaments is separately packaged.

30. A method of preparing a combination effective in the treatment of reactive arthritis or osteoarthritis, said method comprising:
combining a pharmaceutically effective amount of at least two of: (i) an antiviral compound, (ii) a broad-spectrum antibiotic, and (iii) an antiprotozoal compound, to thereby provide an anti-arthritic or anti-osteoarthritic combination.

31. The method of claim 30, wherein said combining step comprises combining each of said compounds into a single administrable formulation.

32. The method of claim 31, wherein said combining step further comprises the addition of one or more pharmaceutically acceptable excipients.

33. The method of claim 31, wherein said single administrable formulation is in a form suitable for oral or parenteral administration.

34. The method of claim 30, wherein said combining step comprises combining each of said compounds into a kit, wherein each of said compounds is for simultaneous, sequential or separate use.

35. A method for the treatment of an inflammatory condition selected from reactive or osteoarthritis and bursitis, said method comprising administering to a mammalian subject suffering from one or more of the following symptoms: stiffness, joint pain, joint tenderness, spine pain, spine tenderness, and fatigue, a therapeutically effective amount of at least two of: (i) an antiviral compound, (ii) a broad-spectrum antibiotic, and (iii) an antiprotozoal compound, over a duration of time effective to result in a diminution of said one or more symptoms.

36. The method of claim 35, wherein said administering is over a duration of time effective to result in substantial elimination of said one or more symptoms.

37. The method of claim 35, comprising administering a therapeutically effective amount of each of (i) an antiviral compound, (ii) a broad-spectrum antibiotic, and (iii) an antiprotozoal compound.

38. The method of claim 35, wherein said administering is by oral or parenteral administration.

39. The method of claim 35, wherein said administering step comprises administering a therapeutically effective amount of a combination of minocycline, metronidazole, and acyclovir.

40. The method of claim 35, wherein said administering step comprises administering a therapeutically effective amount of a combination of doxycycline, metronidazole, and acyclovir.

41. The method of claim 35, wherein said administering step comprises administering a therapeutically effective amount of a combination of minocycline, metronidazole, and valacyclovir.

42. The method of claim 35, wherein said administering step comprises administering a therapeutically effective amount of a combination of doxycycline, metronidazole, and valacyclovir.

* * * * *

SEQUENCE LISTING

<160> NUMBER OF SEQ ID NOS: 1

<210> SEQ ID NO 1
<211> LENGTH: 36
<212> TYPE: PRT
<213> ORGANISM: enfuvirtide

<400> SEQUENCE: 1

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
            35